(12) United States Patent
Bitjonck

(10) Patent No.: US 11,992,318 B2
(45) Date of Patent: May 28, 2024

(54) DIAGNOSTIC LAB-ON-A-CHIP DEVICE

(71) Applicant: Celestin B. Bitjonck, Fort Worth, TX (US)

(72) Inventor: Celestin B. Bitjonck, Fort Worth, TX (US)

( * ) Notice: Subject to any disclaimer, the term of this patent is extended or adjusted under 35 U.S.C. 154(b) by 0 days.

(21) Appl. No.: 17/812,327

(22) Filed: Jul. 13, 2022

(65) Prior Publication Data

US 2024/0016431 A1  Jan. 18, 2024

(51) Int. Cl.
*A61B 5/20* (2006.01)
*A61B 5/00* (2006.01)
(Continued)

(52) U.S. Cl.
CPC ............ *A61B 5/207* (2013.01); *A61B 5/0022* (2013.01); *A61B 5/7275* (2013.01); *A61B 10/0038* (2013.01); *A61B 10/007* (2013.01); *G16H 10/60* (2018.01); *G16H 40/67* (2018.01); *G16H 50/20* (2018.01); *A61B 2090/063* (2016.02);
(Continued)

(58) Field of Classification Search
CPC ..... A61B 5/0022; A61B 5/207; A61B 5/7275; A61B 10/007; A61B 10/0038; A61B 2090/063; A61B 2560/0242; A61B 2560/0462; G16H 10/60; G16H 40/67; G16H 50/20
See application file for complete search history.

(56) References Cited

U.S. PATENT DOCUMENTS 11,064,886 B2    7/2021    Prokopp
2005/0021605 A1    1/2005    Davies et al.
(Continued)

FOREIGN PATENT DOCUMENTS

CN    209136623 U    7/2019
DE    3402488 C2    8/1989
(Continued)

OTHER PUBLICATIONS

Li, X., Wei, Y., & Wang, Z. (2018). MicroRNA-21 and hypertension. Hypertension Research, 41(9), 649-661. https://doi.org/10.1038/s41440-018-0071-z (Year: 2018).*
(Continued)

*Primary Examiner* — Christine H Matthews
*Assistant Examiner* — Marc D. Honrath
(74) *Attorney, Agent, or Firm* — PERKINS COIE LLP

(57) ABSTRACT

A diagnostic hub located in a toilet receives a wireless signal from a mobile device of a user and determines that the user is proximate to the toilet based on the wireless signal. An identification of the user is determined based on the wireless signal. A geolocation of the diagnostic hub is determined. Sensor data generated by biometric sensors and environmental sensors is received. The diagnostic intakes a mixture of water and urine from the toilet into an intake chamber of the diagnostic hub through an inlet line or one or more openings in a housing of the diagnostic hub. A lab-on-a-chip of the diagnostic hub executes a biochemical assay on a fluid volume of the mixture using a reagent. Substance levels present in the urine are determined based on the biochemical assay. Results based on the substance levels are determined, indicating a diagnosis of one or more diseases or medical conditions.

20 Claims, 8 Drawing Sheets

(51) Int. Cl.
    *A61B 10/00*     (2006.01)
    *G16H 10/60*     (2018.01)
    *G16H 40/67*     (2018.01)
    *G16H 50/20*     (2018.01)
    *A61B 90/00*     (2016.01)

(52) U.S. Cl.
    CPC ............... *A61B 2560/0242* (2013.01); *A61B 2560/0462* (2013.01)

(56) References Cited

U.S. PATENT DOCUMENTS

| | | | |
|---|---|---|---|
| 2008/0274495 | A1 | 11/2008 | Jumonville et al. |
| 2014/0094391 | A1* | 4/2014 | McDevitt ........... A61B 10/0051 600/572 |
| 2016/0000378 | A1 | 1/2016 | Hall et al. |
| 2017/0322197 | A1* | 11/2017 | Hall ..................... G01N 33/493 |
| 2018/0372717 | A1* | 12/2018 | Tu .................... G01N 35/00732 |
| 2019/0231240 | A1 | 8/2019 | Short et al. |
| 2021/0074390 | A1* | 3/2021 | Peesapati ............... G16H 10/60 |
| 2021/0134433 | A1 | 5/2021 | Burd et al. |
| 2021/0325389 | A1* | 10/2021 | Hall ....................... G16H 15/00 |
| 2022/0211332 | A1* | 7/2022 | Demmer ............ A61B 5/02405 |

FOREIGN PATENT DOCUMENTS

| | | | | |
|---|---|---|---|---|
| DE | 69117229 | T2 | 9/1996 | |
| DE | 69520850 | T2 | 3/2002 | |
| DE | 60126448 | T2 | 3/2007 | |
| DE | 102010061035 | B4 | 10/2012 | |
| KR | 20220009572 | A * | 1/2022 | ........... A61B 5/0002 |
| WO | 2009035599 | A1 | 3/2009 | |
| WO | 2009107988 | A2 | 9/2009 | |
| WO | 2012077933 | A2 | 6/2012 | |
| WO | 2012105748 | A1 | 8/2012 | |
| WO | WO-2012105748 | A1 * | 8/2012 | ........... G01N 33/493 |
| WO | WO-2021175944 | A1 * | 9/2021 | ......... A61B 10/0012 |

OTHER PUBLICATIONS

Written Opinion and Search Report dated Apr. 11, 2023 of PCT/US2022/075780 (10 pages).

* cited by examiner

```
┌─────────────────────────────────────────────────────────────────┐
│ Receive, by a wireless transceiver, signals emitted by a user   │
│ device in proximity to a diagnostic hub and indicating an       │
│ identity of the user device                                      │
│                              404                                 │
└─────────────────────────────────────────────────────────────────┘
                                │
┌─────────────────────────────────────────────────────────────────┐
│ Determine that a user is in proximity to the diagnostic hub     │
│ based on the signals                                             │
│                              408                                 │
└─────────────────────────────────────────────────────────────────┘
                                │
┌─────────────────────────────────────────────────────────────────┐
│ Cause the diagnostic hub to intake a mixture of water and urine │
│ from a bowl of a toilet into a housing of the diagnostic hub    │
│ located on a surface of the bowl and proximate to a water level │
│ in the bowl or at least partially submerged in the bowl         │
│                              412                                 │
└─────────────────────────────────────────────────────────────────┘
                                │
┌─────────────────────────────────────────────────────────────────┐
│ Analyze the mixture using a lab-on-a-chip (LoC) of the          │
│ diagnostic hub by conducting a biochemical assay on the mixture │
│ using a reagent stored in the diagnostic hub, determining a     │
│ plurality of substance levels present in the urine based on the │
│ biochemical assay, and generating results based on the          │
│ plurality of substance levels, the results indicating one of a  │
│ diagnosis of a disease or medical condition, a likelihood that  │
│ the user will develop the disease or medical condition, or a    │
│ change in a level of the disease or medical condition in the    │
│ user                                                             │
│                              416                                 │
└─────────────────────────────────────────────────────────────────┘
                                │
┌─────────────────────────────────────────────────────────────────┐
│ Transmit, using the wireless transceiver, the results to at     │
│ least one of the device, a healthcare provider device, or a     │
│ cloud server                                                     │
│                              420                                 │
└─────────────────────────────────────────────────────────────────┘
```

*FIG. 4*

DIAGNOSTIC LAB-ON-A-CHIP DEVICE

TECHNICAL FIELD

The present document is generally related to automated and remote diagnostic equipment.

BACKGROUND

Traditionally, clinical laboratory testing is used for providing medical diagnoses. However, diagnostic errors occurring in clinical laboratory testing can lead to missed, delayed, or wrong diagnoses, and in some cases to patient deaths. Recent reports reveal that diagnostic and medical errors remain unacceptably high, despite traditional patient safety initiatives. Adverse events can be related to errors occurring before or after a surgical procedure, as well as technical surgical errors during an operation. For example, adverse events can occur due to (i) a breakdown in communication within and among the surgical team, care providers, patients, and their families; (ii) delays in diagnosis or failure to diagnose; and (iii) delays in treatment or failure to treat. The risks of diagnostic errors can include hemorrhaging, high blood pressure, a rise or fall in body temperature, etc. Such adverse events can further lead to medical errors, infections, underlying physical health conditions of the patient, reactions to anesthetics or other drugs, etc. Conventional clinical laboratory testing methods are typically insufficient to prevent diagnostic delays, diagnostic errors, and adverse medical events.

BRIEF DESCRIPTION OF THE DRAWINGS

FIG. 4 is a flow diagram illustrating an example process for performing medical diagnostic tests, in accordance with one or more embodiments.

DETAILED DESCRIPTION

Figure 1:
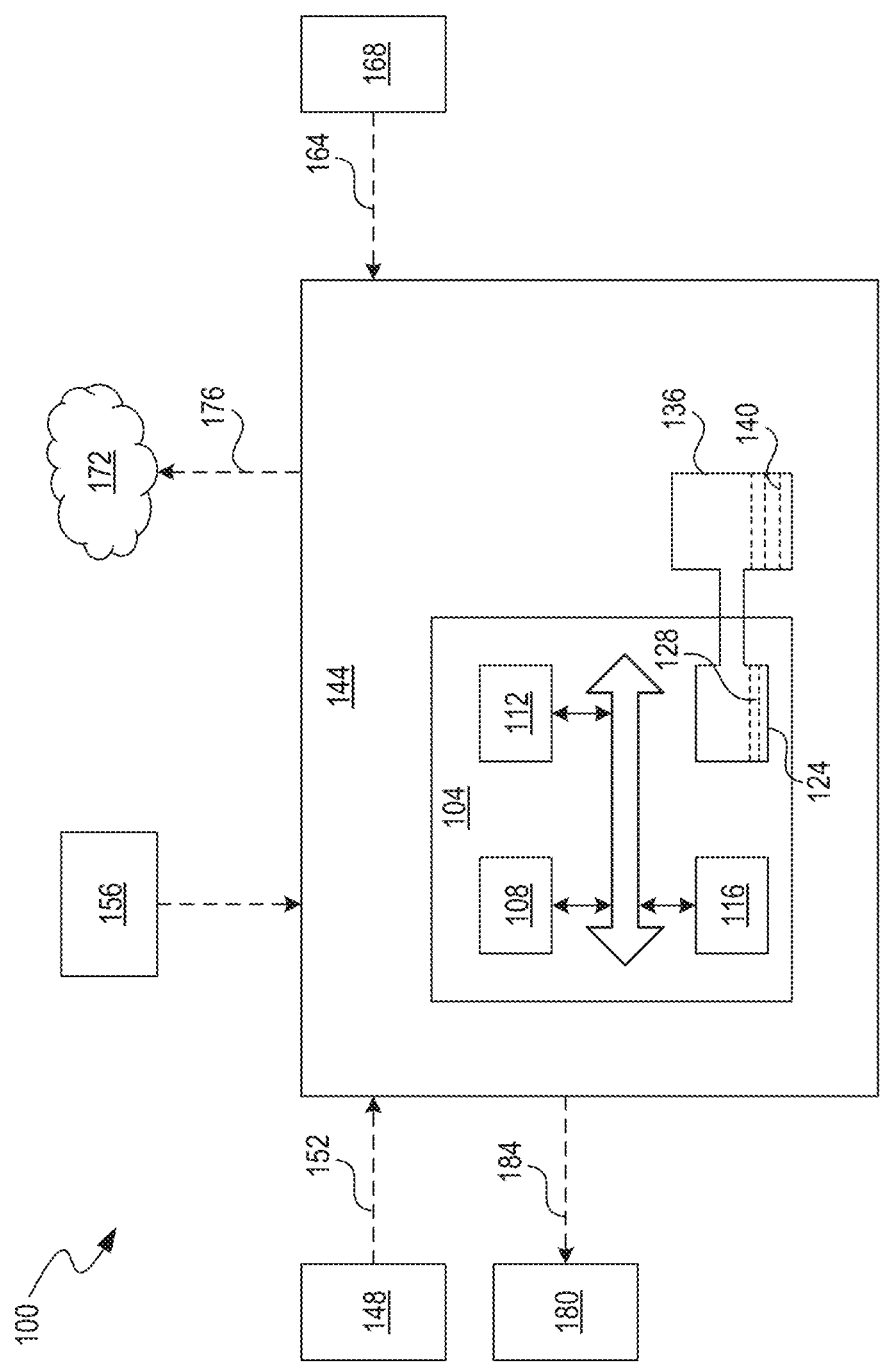
FIG. 1 is a block diagram illustrating an example system for performing medical diagnostic tests for remote medicine, in accordance with one or more embodiments.

Embodiments are described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "512") can implement components, operations, or structures (e.g., "512a") described as a single instance. Further, plural instances (e.g., "512") refer collectively to a set of components, operations, or structures (e.g., "512a") described as a single instance. The description of a single component (e.g., "512a") applies equally to a like-numbered component (e.g., "512b") unless indicated otherwise. These and other aspects, features, and implementations can be expressed as methods, apparatuses, systems, components, program products, means, or steps for performing a function, and in other ways. These and other aspects, features, and implementations will become apparent from the following descriptions, including the claims.

Medical errors have been estimated to be the third leading cause of death in the United States, with up to one-third of these cases associated with diagnostic errors. A 2014 study by Singh et al. derived estimates from large observational studies of the U.S. population to determine that 1 in 20 adults is affected by a diagnostic error during their lifetime. In 2015, the National Academy of Medicine (NAM), formerly the Institute of Medicine, published a report, *Improving Diagnosis in Health Care*, highlighting the critical need to understand and address shortcomings in the diagnostic process (Ira M. Lubin, 2021). The process of arriving at an accurate diagnosis often involves many steps in a complex system, and errors can occur at any step along the way. It is perhaps most frustrating and tragic, however, when the ball is dropped in the final step: the patient presents in a timely manner, the clinical evaluation is performed well, appropriate tests are ordered, the tests are performed correctly within an appropriate interval, the results are diagnosed and transmitted to a clinician, and then the final step—the clinician and patient executing a treatment plan-does not take place (Shapiro, 2013).

Laboratory diagnostic tests, procedures, office visits, and hospitalizations are often billed for an amount that exceeds what providers expect from an insurance company in order to obtain the maximum amount possible from the insurance company. Therefore, patients without insurance, or for whom the insurance claim is denied, are often billed for five to ten times what an insurance company would pay. Moreover, diagnostic errors associated with the failure to follow up on abnormal diagnostic studies ("missed results") are a potential cause of treatment delay and a threat to patient safety. Little data exists concerning the frequency of missed results and associated treatment delays within the Veterans Health Administration (Terry L. Wahls, 2007).

In recent years, people have expressed a growing desire to obtain more information about and have greater control of matters related to their health care. For example, a person may live in a geographical region where a visit to a health care facility requires considerable travel. In another example, an individual may live in an area having ready access to health care facilities, but the individual desires a greater ability to monitor various aspects of their own health. For the reasons stated herein, which will become apparent to those skilled in the art upon reading and understanding the specification, there is a need in the art for improved systems and methods for mobile and reconfigurable personal health monitoring, remote and automated diagnostic testing, and devices to perform the same.

The embodiments disclosed herein describe methods, apparatuses, and systems for performing medical diagnostic tests for remote medicine. Devices and methods for determining health data are disclosed. Some devices and methods operate using analysis of human urine and/or feces obtained from a toilet in normal daily usage. The devices disclosed are portable and can travel with the owner wherever he/she moves. The diagnostic procedures disclosed can be performed in a short amount of time (e.g., less than 30 minutes) and provide a detailed health profile to users whenever they desire to receive a diagnosis.

In embodiments, a computer-implemented method for performing remote medical diagnostic testing includes receiving short-range wireless communication signals emitted by a user device carried by or worn by a user in proximity to a diagnostic hub located proximate to a toilet. A short-range wireless communication signal is received by a wireless transceiver of the diagnostic hub and indicates an identity of the user device. Using one or more computer processors of the diagnostic hub, it is determined that the user is in proximity to the toilet based on the short-range wireless communication signals. The one or more computer processors are communicably coupled to the wireless transceiver. Using the one or more computer processors, identification (ID) of the user is determined based on the short-range wireless communication signals and the identity of the user device.

In embodiments, the one or more computer processors determine a geolocation of the diagnostic hub by at least either analyzing location signals received by a geolocation receiver of the diagnostic hub or analyzing location information embedded in the short-range wireless communication signals. The location signals indicate the geolocation, and the one or more computer processors are communicably coupled to the geolocation receiver. The location information independently indicates the geolocation. Using the one or more computer processors, sensor data generated by multiple biometric sensors and environmental sensors is evaluated. The multiple biometric sensors and environmental sensors are communicably coupled to the diagnostic hub. The diagnostic hub intakes a mixture of water and urine and/or feces from a bowl of the toilet into an intake chamber of the diagnostic hub through an inlet line or one or more openings in a housing of the diagnostic hub. The housing is located proximate to a water level in the toilet bowl or at least partially submerged in the toilet bowl. The diagnostic hub is enclosed by the housing.

In embodiments, a lab-on-a-chip of the diagnostic hub performs an analysis of the mixture by biosensing one or more micro ribonucleic acid (miRNA) biomarkers in the mixture using one or more biosensors of the lab-on-a-chip. For example, the lab-on-a-chip determines a diagnosis of one or more diseases or medical conditions of a user from the one or more miRNA biomarkers. The lab-on-a-chip can determine a likelihood that the user will develop a disease or medical condition or a change in a level of the disease or medical condition in the user.

In some optional embodiments, a DNA sensor of the diagnostic hub determines one or more components of the user's deoxyribonucleic acid (DNA) present in the mixture of water and urine and/or feces. In some embodiments, no DNA sensor is used and the user's DNA is not analyzed. Only a urine sensor is used and the biochemical analysis is performed only on the urine. In some optional embodiments, a urine analysis performed using miRNA biosensing in the diagnostic hub determines one or more components of the user's urine present in the mixture of water and urine.

Using a lab-on-a-chip of the diagnostic hub, the mixture of water and urine and/or feces is analyzed by performing a biochemical assay on a fluid volume of the mixture of water and urine and/or feces using a reagent stored in the diagnostic hub. Results of the remote medical diagnostic testing are generated based on the biochemical assay and the one or more components of the user's microRNA. The results indicate at least one of a diagnosis of a disease or medical condition, a likelihood that the user will develop the disease or medical condition, a change in a level of the disease or medical condition in the user, or a plurality of substance levels present in the urine. Using the one or more computer processors, the results of the remote medical diagnostic testing are correlated to the sensor data generated by the multiple biometric sensors and environmental sensors. The results of the remote medical diagnostic testing tagged by the user ID and the geolocation are transmitted to a mobile device, a health care provider's device, or a cloud server.

The advantages and benefits of the methods, systems, and apparatuses disclosed herein include reducing unnecessary hospital "length of stay," health care costs, and delays in reviewing test results. The diagnostic systems disclosed use computer networks, the Internet, intranets, and supporting technologies to implement a cost-effective technology to collect, transmit, store, analyze, and use patient information in electronic formats. As a result, automated systems can use the embodiments to collect and analyze vast amounts of information, resulting in early diagnoses. The disclosed methods reduce the amount of noise and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to medical professionals.

The urine analysis methods disclosed provide a broader diagnosis concerning the actual state of health of the patient's body compared to the analysis of only temperature, pulse rate, blood pressure, or vital signs. The early diagnosis of possible illnesses provided by the disclosed methods can considerably increase the chances of a cure. The disclosed embodiments offer a non-invasive way to collect and analyze urine and/or feces and provide results in less than 30 minutes or an hour. Tests on feces can detect COVID-19. Moreover, the urine tests disclosed make it possible to measure components, such as microRNA, glucose, protein, hormones, vitamins, or occult blood, in order to find indications of possible diabetes mellitus, nephrosis, hepatitis or other inflammatory diseases, a stone or tumor in the kidneys, bladder or urethra, or prostatitis. The disclosed diagnostic system provides the ability to detect the presence of various illnesses in the early stages, including cancer, cardiovascular disease, malaria, lupus, ovarian cancer, and the like. Significantly, there is no redesign to the style or implementation of the different types of toilets that depend on the culture and area of location. The embodiments can be readily implemented on planes or buses, and in restaurants, hospitals, public places, or homes.

In addition, the advantages of the convolutional neural network (CNN) used for machine learning in the disclosed embodiments include the obviation of feature extraction and the use of shared weight in convolutional layers, which means that the same filter (weights bank) is used for each node in the layer; this both reduces memory footprint and improves performance. The resulting outputs can be selected and correlated to generate one or more diagnoses based on, for example, patient information (e.g., age, condition, status, etc.), accuracy scores for the individual values, ML models, and/or various combinations thereof. The methods disclosed herein can correlate data to reference cases to identify similar individuals with known conditions. Then the reference cases (and the combined measurements) are used to diagnose an individual's condition. Accordingly, the systems and methods disclosed herein provide an accurate assessment of the individual's condition.

FIG. 1 is a block diagram illustrating an example system 100 for performing medical diagnostic tests for remote medicine, in accordance with one or more embodiments. The system 100 includes a toilet 144, a diagnostic device, a mobile device 148, and sensors 168. In embodiments, the system 100 is implemented using components of the example computer system 800 illustrated and described in more detail with reference to FIG. 6. Particular entities, for example, the ML system 700 or the ML model 716, are used to implement at least a portion of the system 100 in other embodiments. The ML system 700 and the ML model 716 are illustrated and described in more detail with reference to FIG. 7. Likewise, embodiments can include different and/or additional components, or be connected in different ways.

In embodiments, the diagnostic device is a diagnostic hub 104 including electronic circuitry, a lab-on-a-chip 116, an intake chamber 124, and a bus for communication between the components of the diagnostic hub 104. In embodiments, the diagnostic device is simply a computer device, a portable device, or a wearable device. The lab-on-a-chip 116 is a device that integrates one or several laboratory functions on a single integrated circuit of only millimeters to a few square centimeters to achieve automation and high-throughput screening. The lab-on-a-chip 116 can handle extremely small fluid volumes down to less than pico-liters. In embodiments, the lab-on-a-chip 116 uses microfluidics to perform analysis. In embodiments, the lab-on-a-chip 116 uses the machine learning methods and system 500 illustrated and described in more detail with reference to FIG. 5 to perform analysis of the mixture 140.

In embodiments, the lab-on-a-chip 116 operates by scaling of single or multiple lab processes down to chip-format. In embodiments, the lab-on-a-chip 116 integrates a sequence of lab processes to perform chemical analysis. The intake chamber 124 is a reservoir or tank within a housing of the diagnostic hub 104. In embodiments, the housing is located on a surface of a bowl 136 of the toilet 144 proximate to a water level in the bowl 136 or at least partially submerged in the bowl 136, such that the mixture 140 can enter the intake chamber 124.

In embodiments, the system 100 performs a computer-implemented method of operating the diagnostic hub 104. The diagnostic hub 104 is located in the toilet 144. A wireless transceiver 108 of the diagnostic hub 104 receives wireless communication signals 152 from a mobile device 148 of a user. The mobile device 148 can be a smartphone, a tablet, a fitness tracker, a smartwatch, etc. The wireless transceiver 108 is an electronic device that is a combination of a radio transmitter and a receiver. The wireless transceiver 108 can both transmit and receive radio waves using an antenna, for communication purposes. The wireless communication signals 152 are radio waves, other electromagnetic waves, or short-range wireless signals. Short-range wireless communication technology is used to communicate wirelessly over shorter distances, such as a few millimeters to several meters. Short-range wireless communication technology includes near field communication (NFC), Zigbee, Bluetooth, Wi-Fi, radio frequency identification (RFID), Z-wave, infrared (IR) wireless, and equivalents. Other types of short-range wireless communication such as 3.84 MHz wireless and minimum-shift keying (MSK) can also be used by the diagnostic hub to communicate with the mobile device 148 and sensors 168.

For example, the wireless communication signals 152 can use NFC (a set of communication protocols for communication between two electronic devices over a distance of 4 cm or less.) NFC devices can act as electronic identity documents or keycards. NFC is based on inductive coupling between two antennas present on NFC-enabled devices—for example, a smartphone and an NFC card-communicating in one or both directions, using a frequency of 13.56 MHz in the globally available unlicensed radio frequency industrial, scientific, and medical (ISM) band and using the ISO/IEC 18000-3 air interface standard at data rates ranging from 106 to 424 kbit/s.

Zigbee is a wireless technology developed as an open global standard to address the unique needs of low-cost, low-power wireless Internet of Things (IoT) networks. The Zigbee standard operates on the IEEE 802.15.4 physical radio specification and operates in unlicensed bands including 2.4 GHz, 900 MHz, and 868 MHz. Bluetooth technology is a high-speed, low-power wireless technology link that is designed to connect phones or other portable equipment together. The Bluetooth specification (IEEE 802.15.1) is for the use of low-power radio communications to link phones, computers, and other network devices over short distances without wires. Wireless signals transmitted with Bluetooth cover short distances, typically up to 30 feet (10 meters). It is achieved by embedding low-cost transceivers into the devices. Wi-Fi is a family of wireless network protocols, based on the IEEE 802.11 family of standards, which are commonly used for local area networking of devices and Internet access, allowing nearby digital devices to exchange data by radio waves. RFID uses electromagnetic fields to automatically identify and track tags attached to objects. An RFID system consists of a tiny radio transponder, a radio receiver, and a transmitter. When triggered by an electromagnetic interrogation pulse from a nearby RFID reader device, the tag transmits digital data back to the reader. Passive tags are powered by energy from the RFID reader's interrogating radio waves. Active tags are powered by a battery and thus can be read at a greater range from the RFID reader, up to hundreds of meters.

Z-Wave is a wireless communications protocol on a mesh network using low-energy radio waves to communicate from appliance to appliance, allowing for wireless control of devices. A Z-Wave system can be controlled via the Internet from a smartphone, tablet, or computer, and locally through a smart speaker, wireless key fob, or wall-mounted panel. IR wireless is the use of wireless technology in devices or systems that convey data through infrared radiation. Infrared is electromagnetic energy at a wavelength or wavelengths somewhat longer than those of red light. The shortest-wavelength IR borders are visible as red in the electromagnetic radiation spectrum; the longest-wavelength IR borders are radio waves.

In embodiments, one or more computer processors 112 determine that the user is proximate to the toilet 144 based on the wireless communication signals 152. The one or more computer processors 112 determine a user identification of the user based on the wireless communication signals 152. For example, the user identification can include a phone number of the mobile device 148, an International Mobile Equipment Identity (IMEI) number of the mobile device 148, a name of the user, a birth date of the user, etc. In embodiments, the one or more computer processors 112 determine a geolocation of the diagnostic hub 104 by analyzing location signals received by a geolocation receiver of the diagnostic hub 104. For example, the geolocation receiver can be a GPS receiver that receives location signals from GPS satellites 156. In embodiments, the one or more computer processors 112 determine a geolocation of the diagnostic hub 104 by analyzing location information embedded in the wireless communication signals 152. For example, the wireless communication signals 152 can include information describing a location of the mobile device 148 based on cellular data of the mobile device 148 or a GPS receiver of the mobile device 148.

In embodiments, the one or more computer processors 112 receive sensor data 164 generated by multiple biometric sensors and environmental sensors 168 communicably coupled to the diagnostic hub 104. Some of the sensors 168 can be located on a fitness tracker or a smartwatch worn by the user. Some of the sensors 168 can be located on the mobile device 148. In embodiments, the sensor data 164 describes a heart rate, a blood pressure, an amount of dissolved oxygen, a respiratory rate, a composition of sweat, a stress level, or a body temperature of the user. Example sensors and sensor data are illustrated and described in more detail with reference to FIG. 2.

In embodiments, the computer processors 112 causes the diagnostic hub 104 to intake a mixture 140 of water and urine and/or feces from the toilet 144 into the intake chamber 124 of the diagnostic hub 104. The mixture 140 enters through an inlet line or one or more openings in a housing of the diagnostic hub 104. For example, a suction device or siphoning device can be used.

In embodiments, the lab-on-a-chip 116 analyzes the mixture 140 by biosensing one or more micro ribonucleic acid (miRNA) biomarkers in the mixture using one or more biosensors. A biosensor is an analytical device, used for the detection of a chemical substance, that combines a biological component with a physicochemical detector. For example, a sensitive biological element (e.g., tissue, microorganism, organelle, cell receptor, enzyme, antibodies, nucleic acid, etc.) can be a biologically derived material or biomimetic component that interacts with, binds with, or recognizes an analyte in the mixture 140. A transducer in the biosensor or in the lab-on-a-chip 116 transforms an input signal into another signal in a physicochemical way, e.g., optical, piezoelectric, electrochemical, electrochemiluminescence etc., resulting from the interaction of the analyte with the biological element. The biosensor connects to associated electronics or signal processors in the lab-on-a-chip 116.

In embodiments, the biosensor is an electrochemical sensor performing impedance spectroscopy for the determination of miR-155. In embodiments, the biosensor used is a four-way junction electrochemical sensor, operating without need for PCR amplification. In other embodiments, a three-mode duplexed sensor or a two-electrode, self-powered biofuel-based sensor is used.

In embodiments, the lab-on-a-chip 116 determines a diagnosis of one or more diseases or medical conditions of a user from the one or more miRNA biomarkers. For example, miRNA expression patterns are altered in patients suffering from chronic lymphocytic leukemia. Further, miRNA expression is found to change during tumorigenesis, and can be used to classify human cancers. Further, miRNAs can be used as biomarkers of diabetes, Alzheimer's Disease, etc. In embodiments, the lab-on-a-chip 116 determines a likelihood that the user will develop a disease or medical condition. For example, miRNA biomarkers can be prognostic, identifying the likelihood of developing specific disease outcomes. In another example, changes in miRNA profiles can be observed early in disease onset, before a pathogen can be directly detected and prior to the onset of seroconversion. An identified and validated COVID-19 miRNA signature can provide differential diagnosis to identify COVID-19 infections from other infections with similar presenting symptoms such as influenza, rhinoviruses or other coronaviruses. Additionally, miRNAs can identify the likelihood of severe vs. mild disease outcomes and also to identify asymptomatic infections.

In embodiments, the lab-on-a-chip 116 determines a change in a level of one or more diseases or medical conditions in the user. For example, a latency period can present a hurdle when a pathogen is present but cannot be detected via routine diagnostic methods. While the patient appears healthy, the pathogen can reactivate at any time, causing clinical disease or shedding infectious material. However, using the embodiments described herein, miRNA expression patterns can be elevated in latent TB infection when compared to active infection or healthy controls. Moreover, miRNAs can be used to identify patients who are cured of TB infection, and to discriminate between resolved and latent infections.

In embodiments, the analysis is performed by the lab-on-a-chip on the mixture using a biochemical reagent. For example, the lab-on-a-chip 116 performs an analytical procedure to detect and quantify cellular processes (e.g., apoptosis, cell signaling) or metabolic reactions. The lab-on-a-chip 116 qualitatively assesses or quantitatively measures various substances and functional activity of biomolecules. The reagent is used to perform chemical reactions controlled by biomolecules to study elements and compounds. Example reagents are illustrated and described in more detail with reference to FIG. 2.

In embodiments, the biosensing is performed using a lateral flow biosensor in the lab-on-a-chip 116. A lateral flow device can be useful for detection of biomarkers because of its lower cost, simplicity, portability and specificity. For example, a multiplexed lateral flow assay can be performed for the simultaneous detection of miR-21, miR-155 and miR-210 in human samples. In embodiments, a target recycling amplification strategy is performed, whereby two sequence specific hairpins are used to amplify the signal without the need for added enzymes. In embodiments, the biosensing is performed using a paper-based microfluidic device (μPAD) in the lab-on-a-chip 116. For example, an integrated patterned μPAD can determine a range of biomarkers using a variety of fabrication and detection strategies. Different μPADs can be used for miRNA extraction and amplification, and for detection of the miRNA. In embodiments, the biosensing is performed using a digital microfluidic (DMF) device in the lab-on-a-chip 116. For example, a DMF device performs software-based electronic control of liquids, reduces the need for tubing and pumps, and reduces sample volumes needed of the mixture 140.

In embodiments, the lab-on-a-chip 116 of the diagnostic hub 104 analyzes the mixture 140 by performing a biochemical assay on a fluid volume 128 of the mixture 140 using a reagent stored in the diagnostic hub 104. For example, the lab-on-a-chip 116 performs an analytical procedure to detect and quantify cellular processes (e.g., apoptosis, cell signaling) or metabolic reactions. The lab-on-a-chip 116 qualitatively assesses or quantitatively measures various substances and functional activity of biomolecules. The reagent is used to perform chemical reactions controlled by biomolecules to study elements and compounds.

Example reagents are illustrated and described in more detail with reference to FIG. 2.

In embodiments, the lab-on-a-chip 116 determines multiple substance levels present in the urine based on the biochemical assay. The substance levels can indicate COVID-19. The substance levels can be levels of acidity (pH). If the acidity is abnormal, the user could have kidney stones, a urinary tract infection (UTI), or another condition. The substance levels can be levels of protein (indicating kidney disease), glucose (a marker for diabetes), white blood cells (indicating infection or inflammation), nitrites (indicating an infection with certain kinds of bacteria), bilirubin (indicating liver problems), or blood (indicating an infection or certain illnesses). For example, the lab-on-a-chip 116 can be used to detect and manage a wide range of disorders, such as urinary tract infection (UTI), kidney disease, or diabetes. The lab-on-a-chip 116 can check the concentration and content of the urine. For example, increased levels of protein in urine can be a sign of kidney disease.

In embodiments, the diagnostic hub 104 generates results of remote diagnostic tests based on the multiple substance levels. The results can indicate a diagnosis of a disease or medical condition of the user. Example diagnosis of diseases or medical conditions are illustrated and described in more detail with reference to FIG. 2. For example, the results can be used to diagnose or rule out a specific disease or condition. An HPV test is an example of this type of test. It can show whether a user has an HPV infection.

In embodiments, the results indicate a likelihood that the user will develop a disease or medical condition. The results can be used for screening. A screening test can show whether a user is at a higher risk for developing a specific disease. It can also reveal whether a user has a disease, even if the user exhibits no symptoms. A pap test is a type of screening test for cervical cancer. For example, when a particular substance level is below the threshold for a disease but is increasing over time and is reaching the threshold, the results can indicate a likelihood that the user will develop the disease. In embodiments, the results indicate a change in a level of the disease or medical condition in the user (e.g., by collecting the results over time and analyzing trends). For example, if a user has already been diagnosed with a disease, the results can indicate whether the individual's condition is getting better or worse. It can also show whether treatment is working.

The results can indicate a substance level of a controlled substance present in the urine that is greater than a threshold substance level. For example, the lab-on-a-chip 116 detects whether one or more prescription or illegal drugs are present in urine. The results can indicate the presence of drugs such as marijuana, cocaine, opiates, methamphetamine, amphetamines, PCP, benzodiazepine, barbiturates, methadone, tricyclic antidepressants, ecstasy, and oxycodone.

In embodiments, the lab-on-a-chip 116 performs a microRNA assay on the mixture 140. The results are generated based on the miRNA assay. The urine analysis can be a branched miRNA assay (a signal amplification assay) or a target amplification assay. For example, a molecular diagnostic assay using a nanoarchitecture in miRNA Biosensing technology for detection of nucleic acid target molecules can be used for diagnosis of viral and bacterial infections and for monitoring disease progression during diagnostic tests. In embodiments, the lab-on-a-chip 116 performs miRNA Biosensing (RNA) analysis. For example, RNA analysis can be used for the detection and quantification of RNA viruses such as HIV and hepatitis C virus, or evaluation of cancer. In some optional embodiments, a urine analysis performed using miRNA biosensing in the diagnostic hub determines one or more components of the user's urine present in the mixture of water and urine.

In embodiments, the computer processors 112 correlate the results to the sensor data 164. For example, correlating a substance level to a heart rate, a temperature of the user, sweat level, etc., can be used for more fine-grained analysis of diseases or medical conditions. In embodiments, the computer processors 112 tags the correlated results with the user identification and the geolocation of the diagnostic hub 104. In embodiments, the wireless transceiver 108 transmits the correlated results 184 tagged by the user identification and the geolocation to the mobile device 148. In embodiments, the wireless transceiver 108 transmits the correlated results 184 tagged by the user identification and the geolocation to a healthcare provider's device 180. In embodiments, the wireless transceiver 108 transmits the correlated results 184 tagged by the user identification and the geolocation to a cloud server 172 for storage, further analysis, or for searching by an entity, such as a hospital.

In embodiments, the computer processors 112 causes the wireless transceiver 108 to increase a frequency of transmitting the correlated results 184 to the health care provider's device 180 or the cloud server 172 responsive to determining a particular indication in the results. For example, the particular indication can be acute symptoms or a prediction of a heart attack or stroke. In embodiments, the computer processors 112 causes the wireless transceiver 108 to increase a frequency of transmitting the correlated results 184 to the health care provider's device 180 or the cloud server 172 responsive to determining a particular correlation of the results to the sensor data. For example, the particular correlation can indicate a rise in COVID-19 detections in a particular geographical area.

In embodiments, the computer processors 112 stores the results in a user health database (e.g., on the cloud server 172). The user health database can include trends 176 recorded over time of the multiple substance levels. The user health database can be the same as or similar to the EHR database 906 are illustrated and described in more detail with reference to FIG. 7. The user health database can include trends 176 recorded over time of diagnoses of diseases or medical conditions. The user health database can include trends 176 recorded over time of likelihoods that the user will develop the diseases or medical conditions. The user health database can include trends 176 recorded over time of changes in levels of the diseases or medical conditions in the user.

Figure 2:
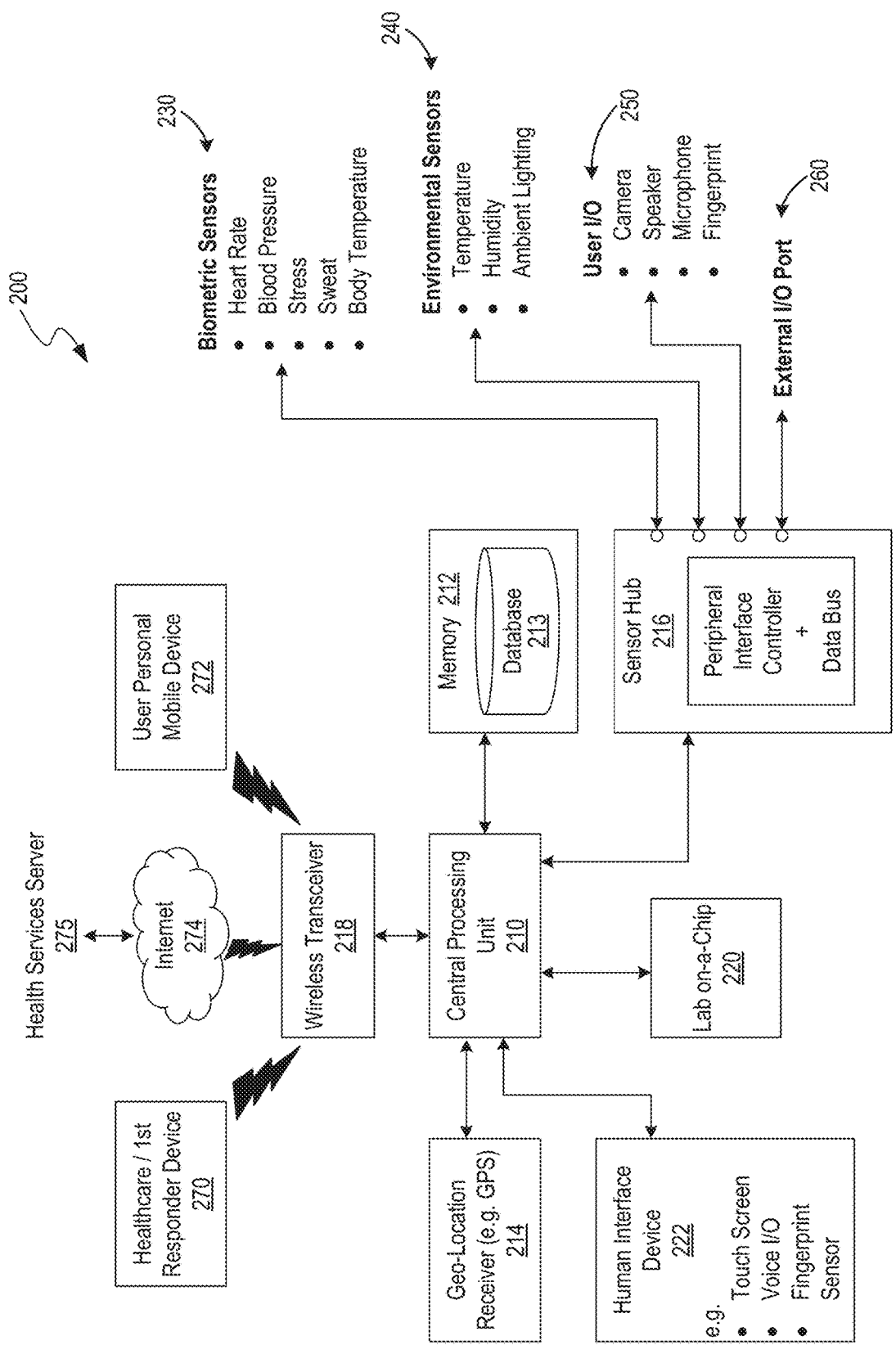
FIG. 2 is a block diagram illustrating an example system for performing medical diagnostic tests for remote medicine, in accordance with one or more embodiments.

FIG. 2 is a block diagram illustrating an example system 200 for performing medical diagnostic tests for remote medicine, in accordance with one or more embodiments. The system 200 includes a 210 and a lab-on-a-chip processing device 220. In embodiments, the system 200 is implemented using components of the example computer system 800 illustrated and described in more detail with reference to FIG. 6. Particular entities, for example, the ML system 700 or the ML model 716, are used to implement at least a portion of the system 200 in other embodiments. The ML system 700 and the ML model 716 are illustrated and described in more detail with reference to FIG. 7. Likewise, embodiments can include different and/or additional steps, or perform the steps in different orders.

The system 200 can be implemented as a wearable health monitoring device. In embodiments, the system 200 includes an assortment of biometric sensors and environmental sensors, each collecting human vital signs. As used in this application, the terms "health care provider" and "health care professional" can refer to any professional that provides a health care service and/or their associated staff including, but not limited to, doctors and physicians (of any medical field or specialization), doctor's office staff, hospital or emergency room staff, physician's assistants, nurses, hygienists, paramedics, emergency medical technicians (EMTs), police and fire-rescue responders, and so forth. The term "first responder" can in turn refer to any health care professional who provides initial care to a person in need. The term "user" as used herein refers to the person from and about whom a health monitoring device senses and collects data. In addition to obtaining vital signs, an application executing on the system 200 can communicate with the toilet 144 to receive urine and/or feces analysis results. The toilet 144 is illustrated and described in more detail with reference to FIG. 1. The system 200 can also perform geolocation tracking of a user's location, with regular recording of the user's vital signs correlated with tracked user locations. In embodiments, the lab-on-a-chip processing device 220 uses the machine learning methods and system 500 illustrated and described in more detail with reference to FIG. 5 to perform analysis of the mixture 140.

In embodiments, the lab-on-a-chip processing device 220 is a specialized processing device with one or more embedded specialized applications configured to analyze biomedical information collected by the biometric sensors 230 and/or environmental sensors 240. In embodiments, the lab-on-a-chip processing device 220 itself does not receive fluids or tangible specimens from the user for analysis. Instead, information provided to lab-on-a-chip processing device 220 is in the form of signals carrying data samples and/or measurements, which can be either analog or digital. In embodiments, the lab-on-a-chip processing device 220 is an assay chip or an integrated chip that enables the development of biological assays on chip. The chip enables on-chip metering, mixing, and the detection of the reaction in a separate chamber. In embodiments, the lab-on-a-chip processing device 220 is a continuous-flow PCT chip or an integrated microfluidic chip that combines the sample preparation (extraction of microRNA) through continuous-flow-PCR. Reagents can be supplied using Mini Luer interfaces. In embodiments, the lab-on-a-chip processing device 220 is an immunoassay chip that combines lab-on-a-chip technology with the advantages of frit-based assays, such as the enrichment of the sample through filtration and specific binding on the frit surface.

In embodiments, the lab-on-a-chip processing device 220 can be a microfluidic device that operates on the urine and/or feces in the toilet. In embodiments, the lab-on-a-chip processing device 220 is a miniaturized "Micro Total Analysis System" that uses urine as a working medium. The processes disclosed herein enable the lab-on-a-chip processing device 220 to be reconfigurable and use reagents for analysis. Once analysis is done, the results can be sent to a cloud server and/or to a requesting device (or a software application). As shown in FIG. 2, the system 200 includes a central processing unit 210 coupled to a memory 212, a geolocation receiver 214, a wireless transceiver 218, the lab-on-a-chip processing device 220, and a sensor hub 216. The sensor hub 216 is coupled to multiple biometric sensors 230 and environmental sensors 240. The system 200 can also include at least one human interface device 222, one or more user input/output (I/O) devices and/or sensors 250, and at least one external I/O port 260.

Central processing unit 210 (or, alternately, processor 210) can be implemented using any suitable mobile processor and/or chip set. In embodiments, central processing unit 210 includes a Qualcomm Snapdragon processor. Memory 212 can be a non-volatile memory that can store, for example, applications executed by processor 210, raw sensor data collected by the sensors 230 and 240, analysis results produced by lab-on-a-chip processing device 220, or other information used by applications executed by processor 210. In embodiments, wireless transceiver 218 implements a two-way radio for communicating data to and from health monitoring device 200. Wireless transceiver 218 can be configured to use a wide range of communications technologies such as, but not limited to: cellular communications, IEEE 802.11 communications (i.e., Wi-Fi), IEEE 802.15.1 communications (i.e., Bluetooth), IEEE 802.15.4 communications (i.e., ZigBee), or other communications standard protocol or combinations thereof. Geolocation receiver 214 can implement one or more mobile geolocation tracking technologies, such as, but not limited to, using Assisted GPS (AGPS) signals from nearby cellular communications towers, to pinpoint a user's geographic location when wearing the health monitoring device 200. Positioning data provided by geolocation receiver 214 can be correlated by processor 210 with sensor 230/240 measurements so that sensed and collected biomedical information and environmental information can be cross-referenced to a user's precise location, revealing exactly where the user was when that information was collected.

Lab-on-a-chip processing device 220 is a specialized processing device with one or more embedded specialized applications configured to analyze biomedical information collected by the biometric sensors 230 and/or environmental sensors 240. In embodiments, the lab-on-a-chip processing device 220 itself does not receive fluids or tangible specimens from the user for analysis. Instead, information provided to lab-on-a-chip processing device 220 is in the form of signals carrying data samples and/or measurements, which can be either analog or digital. In embodiments, the lab-on-a-chip processing device 220 is an assay chip or an integrated chip that enables the development of biological assays on a chip. The chip enables on-chip metering, mixing, and the detection of the reaction in a separate chamber. In embodiments, the lab-on-a-chip processing device 220 is a continuous-flow polymerase chain reaction (PCR) chip or an integrated microfluidic chip that combines the sample preparation (extraction of DNA) and amplification of the DNA through continuous-flow-PCR. Reagents can be supplied using Mini Luer interfaces. In embodiments, the lab-on-a-chip processing device 220 is an immunoassay chip that combines lab-on-a-chip technology with the advantages of frit-based assays, such as the enrichment of the sample through filtration and specific binding on the frit surface. In some optional embodiments, a urine analysis performed using miRNA biosensing in the diagnostic hub determines one or more components of the user's urine present in the mixture of water and urine.

Lab-on-a-chip processing device 220 evaluates the raw biometric information to produce virtual biomedical lab results that can then be correlated against results associated with known health risks or conditions. While evaluations performed by lab-on-a-chip processing device 220 can be performed based on data from a single sensor, other evaluations can use data compiled by multiple sensors. Thus, lab-on-a-chip processing device 220 can input an array or vector of data from multiple sensors and perform its analysis from the information available from that array or vector.

Virtual biomedical lab results output from the lab-on-a-chip processing device 220 are received by software executing on processor 210. In embodiments, the results are stored into a personal health database 213 in memory 212 to record a health history and profile for the user. A user can access personal health database 213 to monitor recent readings and analysis results and trends 176 over time. The trends 176 are illustrated and described in more detail with reference to FIG. 1. In other embodiments, personal health database 213 and/or memory 212 includes a database of general medical information that the user can query. In some implementations, results of queries to the database of general medical information can highlight information particularly relevant or applicable to the user based on information stored in the health history and profile.

Raw biometric and environmental sensor data, geolocation data, and other collected information can also reside on memory 212. In some embodiments, raw data can reside on memory 212 until such time that it is processed by lab-on-a-chip processing device 220 and/or uploaded off of health monitoring device 200. Processor 210 can also further analyze the virtual biomedical lab results and in some instances correlate those results against collected geolocation and environmental information. That is, the lab-on-a-chip processing device 220 can produce time- and location-correlated virtual biomedical lab results based on time-stamped data from the multiple sensors and the geolocation receiver 214. For example, raw sensor and geolocation data can be time-stamped when collected and the virtual biomedical lab results can also include information regarding the time period over which the raw data used to produce the result was collected. In that way, the occurrence of acute conditions detected by the lab-on-a-chip processing device 220 can be associated (using applications running on processor 210) with where the user was at the time the acute condition was occurring, and the environmental conditions the user was exposed to at that time.

Processor 210 can implement multiple different applications, enabling the user and/or health care professionals to use information residing in memory 212 in many different ways. In embodiments, a user access application provides the user of the health monitoring device 200 with a history of collected data and virtual biomedical lab results. In embodiments, the user can interface with this application via a human interface device 222 that can be integrated with the health monitoring device 200. For example, human interface device 222 can include a touch screen that displays information and allows the user to interact with the user access application. Human interface device 222 can further include, for example, a microphone or speaker to permit voice interactions with the user access application (or other applications) executed by processor 210 and/or communications with health care professionals via a wireless connection.

In embodiments, human interface device 222 includes a fingerprint sensor for authenticating the user. In some embodiments, the functionality of the human interface device 222 is instead implemented via a user personal mobile device 272 in communication with health monitoring device 200 via wireless transceiver 218. The user can pair their personal mobile device (such as a smartphone, tablet, or laptop) with health monitoring device 200 via a wireless connection and an application running on the user personal mobile device 272 to operate the user access application (or other applications) executed by processor 210. In some embodiments, when either raw sensor data or virtual biomedical lab results meet certain conditions indicating an urgent health threat, the user access application can provide the user with a visual, audible, and/or tactile alarm indicating the nature of the threat and recommended remedial actions the user should take.

In embodiments, the processor 210 determines a geolocation of the user by analyzing location signals received by the geolocation receiver 214 or analyzing location information received from the personal mobile device 272. The processor 210 can correlate the diagnostic results to the geolocation and tag the correlated results with the geolocation. Information can be presented to the user in a manner that illustrates, in textual or graphical form (for example, superimposed on a map), critical statistics correlated with the geolocation data. For example, the system 200 can indicate that a user's blood pressure and stress levels have a pattern of being elevated while at work, or during a commute, or under other environmental conditions. Similarly, other patterns of biometric parameters, and combinations of biometric parameters, can indicate specific health conditions recognizable to the lab-on-a-chip processing device 220. The user can use such information provided by the system 200 to decide whether to seek medical services for a condition, to better focus their discussion with their medical service provider, and/or provide collected data to their medical service provider. In embodiments, the lab-on-a-chip processing device 220 is configured to provide dietary recommendations based on analysis performed by the lab-on-a-chip processing device 220.

In embodiments, a remote health care monitor application executes on central processing unit 210. The remote health care monitor application uploads selected health information (referred to herein as monitored health information) from memory 212 to a remote health services server 275 accessible by the user, the user's health care provider, and/or others such as, but not limited to, insurance companies. Uploading of data can be done through a wireless connection to the Internet 274 established by wireless transceiver 218 and performed on either a scheduled basis or a condition/event basis. For example, a user's health care provider can schedule the system 200 to upload data to the health services server 275 once per day, but if certain vital sign thresholds (as sensed by biometric sensors 230) are exceeded, or an adverse virtual biomedical lab result is produced by the lab-on-a-chip processing device 220, these occurrences can trigger an immediate or more frequent uploading of data. In some embodiments, the remote health care monitor application uses a two-way voice and/or video communication functionality of the lab-on-a-chip processing device 220 to permit a health care provider to quickly communicate with the user when uploaded data indicates a condition requiring prompt attention.

In embodiments, an emergency access application executes on central processing unit 210. The emergency access application permits a first responder to collect relevant and accurate vital health information about the user when responding to an urgent situation. For example, a first responder would typically obtain a current set of vital signs when coming to the aid of a user. The emergency access application could provide additional information to the first responder regarding vital signs for a period prior to the first responder's arrival. In addition, the first responder could have access to other raw data, virtual biomedical lab results, or other information made available through the emergency access application.

In embodiments, the user, through preference settings, decides what information is immediately available to first responders from the device. For example, a datalink established via the wireless transceiver 218 or other external I/O port 260 can be used to communicate information stored in the device to such health care providers to allow them to make better-informed decisions. In embodiments, first responders can carry monitoring equipment that performs a handshake and establishes a communication link with the health monitoring device 200 when the monitoring equipment and health monitoring device 200 come within a threshold proximity of each other. The first responders can then access the emergency access application and query the memory 212 of device 200 using their monitoring equipment to obtain relevant health information about the user.

Embodiments use a sensor hub 216 that provides both a peripheral interface controller (PIC) and a data bus that facilitates the communication of data between sensors and other peripherals connected to sensor hub 216 and central processing unit 210. In some embodiments, the complement of biometric sensors 230 and environmental sensors 240 available to collect data is reconfigurable and can be tailored to health concerns specific to the user. Accordingly, sensor hub 216 can provide plug-and-play connectivity permitting the user to readily remove, install, and/or replace one or more of the biometric sensors 230 and environmental sensors 240, and the new sensors will identify themselves while health monitoring device 200 self-configures to use the new configuration.

In some implementations, an external sensor or peripheral device can be coupled to sensor hub 216 via an external I/O port 260. Also, by using replaceable sensors that easily couple to and de-couple from sensor hub 216, sensors can be replaced with those using improved technologies when such innovations become available. As mentioned above, the complement of biometric sensors 230 and environmental sensors 240 installed in a health monitoring device 200 can be varied and reconfigured to customize the device to the needs of the user. Raw data collected by these sensors can be stored in memory 212 until used or uploaded as mentioned above. In some embodiments, memory 212 can store at least several days of data.

Environmental sensors 240 can include, but are not limited to, ambient temperature, humidity, ambient lighting, or sensors for other environmental conditions that may be relevant to the user's health. As mentioned above, raw data from the environmental sensors 240 can be time-stamped (for example, when generated by the respective sensor, or when received by central processing unit 210) so that the environmental conditions to which a user is exposed can be correlated with other data and/or aligned along a timeline with other data collected from other sensors.

Biometric sensors 230 can include, but are not limited to, sensors which can measure or evaluate heart rate, blood pressure, dissolved oxygen, respiratory rates, composition or characteristics of user sweat, stress levels, body temperature, and/or user DNA. Raw data from the biometric sensors 230 can be time-stamped in the same manner as described above for the environmental sensors 240 and can be cross-correlated with geolocation data from geolocation receiver 214. While some biometric sensors 230 can sense user health parameters by using electrical or optical observations or stimulus, other biometric sensors 230 may need to collect micro fluids or other user specimens to provide data used by the lab-on-a-chip processing device 220. In the latter case, the biometric sensors 230 may be removable so that they can be periodically flushed and cleaned, or they may be replaceable, or they otherwise may include replaceable filters or components that can be swapped out as necessary.

In embodiments, at least one of the biometric sensors 230 includes an electronic DNA sensor chip configured to identify components of the user's DNA. For example, such an electronic DNA sensor chip can include a complementary metal oxide semiconductor (CMOS)-based DNA sensor, an AC electro-osmosis (ACEO) chip, or a label-free impedimetric DNA sensing chip. In embodiments, the CMOS-based DNA sensor is implemented for the electrical detection of DNA hybridization. The CMOS-based DNA sensor detects the difference of capacitance through the integration of current mismatch of capacitance between reference electrodes functionalized with only single-stranded DNA and sensing electrodes bound with complementary DNA strands specifically. In embodiments, an ACEO chip is part of the lab-on-a-chip processing device 220 and performs a heterogeneous immunoassay. For example, the DNA sensor chip detects the presence of an analyte or measures its concentration.

The electronic DNA sensor chip can communicate raw data to the lab-on-a-chip processing device 220, which in turn can integrate that information into its evaluation for producing virtual biomedical lab results. Because different electronic DNA sensors can be tuned or configured to analyze different segments of a human genome, the relevant DNA sensor can be installed or swapped out depending on conditions of concern. The DNA analysis performed by the electronic DNA sensor in cooperation with the lab-on-a-chip processing device 220 can ascertain whether certain pre-existing conditions are present and can be used to flag risks and/or can be factored into any analysis performed by the lab-on-a-chip processing device 220.

A user can also activate the lab-on-a-chip processing device 220 to input collected user DNA data to help the user make an informed decision when they do not have access to their health care provider. For example, the lab-on-a-chip processing device 220 can include a pharmacogenetics application that considers potentially relevant drug metabolic pathways which can affect the user's individual responses to a drug based on genetic information obtained through the electronic DNA sensor. For example, a user can query health monitoring device 200 when selecting an over-the-counter product, or before using a prescribed product, as to whether there are concerns or risks the user should be aware of when using the product.

In some embodiments, the biometric sensors 230 can include one or both of a sweat sensor and/or a stress sensor. A sweat sensor can, for example, analyze body chemistry via the user's perspiration to detect potential exposure to a dangerous agent or an infectious disease. For example, a sweat sensor can detect metabolites and electrolytes, sodium, potassium, glucose, lactate, or other sweat components that are relevant to health. The sweat sensor can be tuned to look for such specific sweat components and send that data to the lab-on-a-chip processing device 220, which can correlate collected sweat data to specific conditions and combine the collected sweat data with other collected parameters to arrive at its results.

A stress sensor can provide data indicating when the user is in a period of stress or duress. In some embodiments, a stress sensor can provide a quantitative measurement of stress based on a combination of heart rate and blood pressure measurements. In other embodiments, a stress sensor can directly measure other physiological indications of stress. For example, in some embodiments, a stress sensor can include a surface stress-based polydimethylsiloxane (PDMS) micro-membrane biosensor. Other stress sensors can detect, from a user's skin surface, an increase in the user's production of hormones. In addition to the biometric sensors 230 and environmental sensors 240, other peripheral user I/O devices can be coupled to sensor hub 216 as shown at peripheral user I/O device 250. These other peripheral user I/O devices can include, but are not limited to, image sensors (i.e., a camera), audio speakers, microphones, and fingerprint sensors.

The data collection performed by the various biometric sensors 230 and environmental sensors 240 and use of other peripheral user I/O devices 250 can be coordinated. For example, when a heart rate or other specified biometric parameters measured by a sensor are determined to exceed a threshold, that condition can cause the processor 210 to activate other sensors to collect additional data that may be relevant to the detected condition. In other embodiments, when the lab-on-a-chip processing device 220 returns virtual biomedical lab results meeting certain conditions, this can cause the processor 210 to activate a specific complement of sensors. In some embodiments, the health monitoring device 200 can incorporate connectivity features that permit conditional communication of measured parameters and/or virtual biomedical lab results to a health services server 275 and/or bring those results to the attention of a health care provider. For example, under normal circumstances, measured parameters and/or virtual biomedical lab results can be wirelessly uploaded to a health monitoring service or physician's system on a daily basis. However, if one or more designated conditions are identified by the lab-on-a-chip processing device 220, the upload frequency can be increased to provide updates more often.

In embodiments, the system 200 is used to determine a user's overall health. Testing can help detect health problems before symptoms appear. In some embodiments, the system 200 can include two-way voice and/or video communication functionality that permits a health care provider to quickly communicate with the user. This functionality can be used to facilitate routine dialogues between a user and a health care provider, and, together with data uploaded from the system 200 to the health care provider, to avoid the need for an office visit. Alternatively, the communications functionality can be used to attempt to reach a user if uploaded data indicates that the user may need prompt medical attention.

In various alternative embodiments, system and/or device elements, method steps, or example implementations described throughout this document (e.g., lab-on-a-chip processing device 220 and processes and applications executed thereon, processor 210 and applications executed thereon, personal health database 213, database of general medical information, first responder device 270, or sub-parts thereof) can be implemented using one or more computer systems, field programmable gate arrays (FPGAs), or similar devices, including a processor coupled to a memory and executing code to realize those elements, processes, or examples, said code stored on a non-transient data storage device. Therefore, other embodiments described herein can include elements consisting of program instructions resident on computer-readable media which, when implemented by such computer systems, enable them to implement the embodiments described herein. As used herein, the term "computer readable media" refers to tangible memory storage devices having non-transient physical forms. Such non-transient physical forms can include computer memory devices such as, but not limited to, punch cards, magnetic disk or tape, any optical data storage system, flash read only memory (ROM), non-volatile ROM, programmable ROM (PROM), erasable-programmable ROM (E-PROM), random access memory (RAM), or any other form of permanent, semi-permanent, or temporary memory storage system or device having a physical, tangible form. Program instructions include, but are not limited to, computer-executable instructions executed by computer system processors and hardware description languages such as Very High Speed Integrated Circuit (VHSIC) Hardware Description Language (VHDL).

Figure 3A:
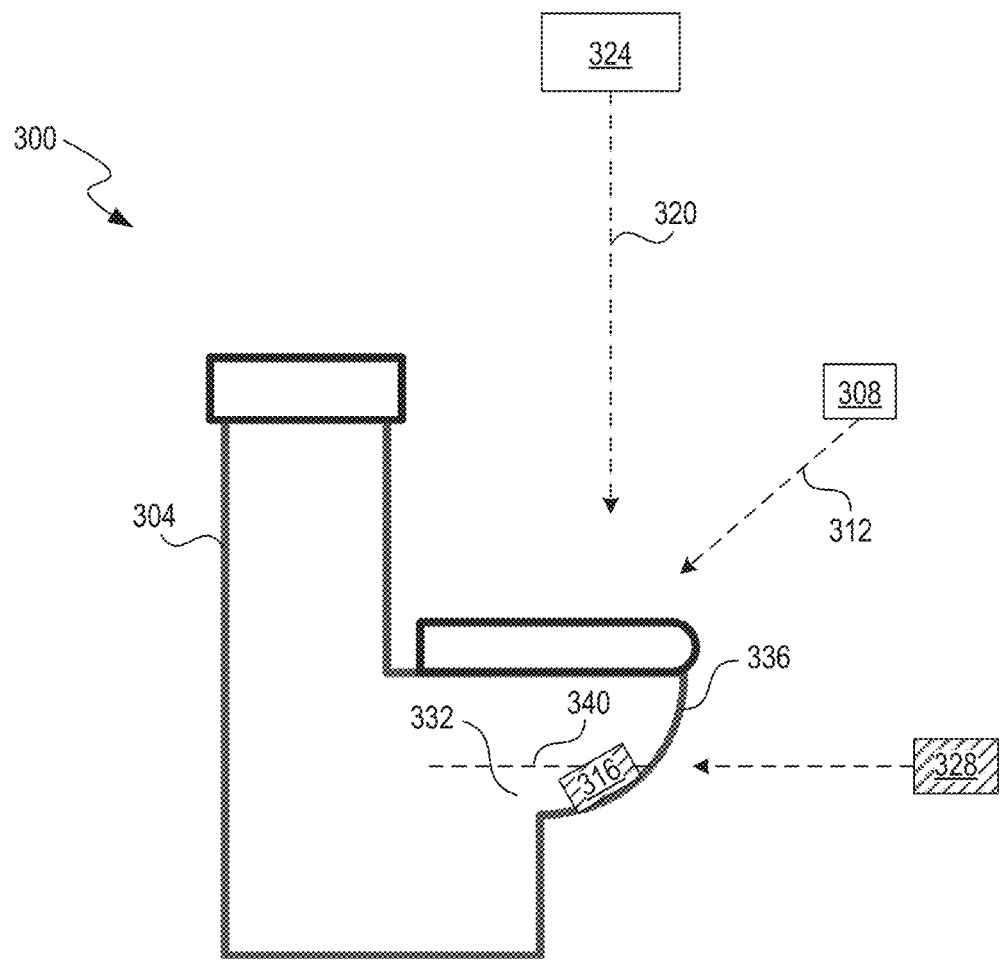
FIG. 3A is a drawing illustrating an example system for performing medical diagnostic tests for remote medicine, in accordance with one or more embodiments.

FIG. 3A is a drawing illustrating an example system 300 for performing medical diagnostic tests for remote medicine, in accordance with one or more embodiments. The system 300 includes a toilet 304, a diagnostic hub 316, a mobile device 308, and sensors 328. In embodiments, the system 300 is implemented using components of the example computer system 600 illustrated and described in more detail with reference to FIG. 6. Particular entities, for example, the ML system 700 or the ML model 716, are used to implement at least a portion of the system 300 in other embodiments. The ML system 700 and the ML model 716 are illustrated and described in more detail with reference to FIG. 7. Likewise, embodiments can include different and/or additional components, or be connected in different ways.

In embodiments, the system 300 performs a computer-implemented method of operating the diagnostic hub 316 located in the toilet 304. A wireless transceiver of the diagnostic hub 316 receives wireless communication signals 312 from the mobile device 308. The diagnostic hub 316 determines that the user is proximate to the toilet 304 based on the wireless communication signals 312. The diagnostic hub 316 determines a user identification of the user based on the wireless communication signals 312. The diagnostic hub 316 determines a geolocation by analyzing location signals 320 (from satellites 324) received by a geolocation receiver of the diagnostic hub 316 or analyzing location information embedded in the wireless communication signals 312. In embodiments, the diagnostic hub 316 uses the machine learning methods and system 500 illustrated and described in more detail with reference to FIG. 5 to perform analysis of the mixture of water and urine and/or feces 332.

In embodiments, the diagnostic hub 316 receives sensor data generated by multiple biometric sensors and environmental sensors 328 communicably coupled to the diagnostic hub 316. The diagnostic hub intakes a mixture of water and urine and/or feces 332 from the toilet 304 into an intake chamber of the diagnostic hub 316 through an inlet line or one or more openings in a housing of the diagnostic hub 316. In embodiments, the housing is located on a surface of a bowl 336 of the toilet 304 proximate to a water level 340 in the bowl 336 or at least partially submerged in the bowl 336.

Figure 3B:
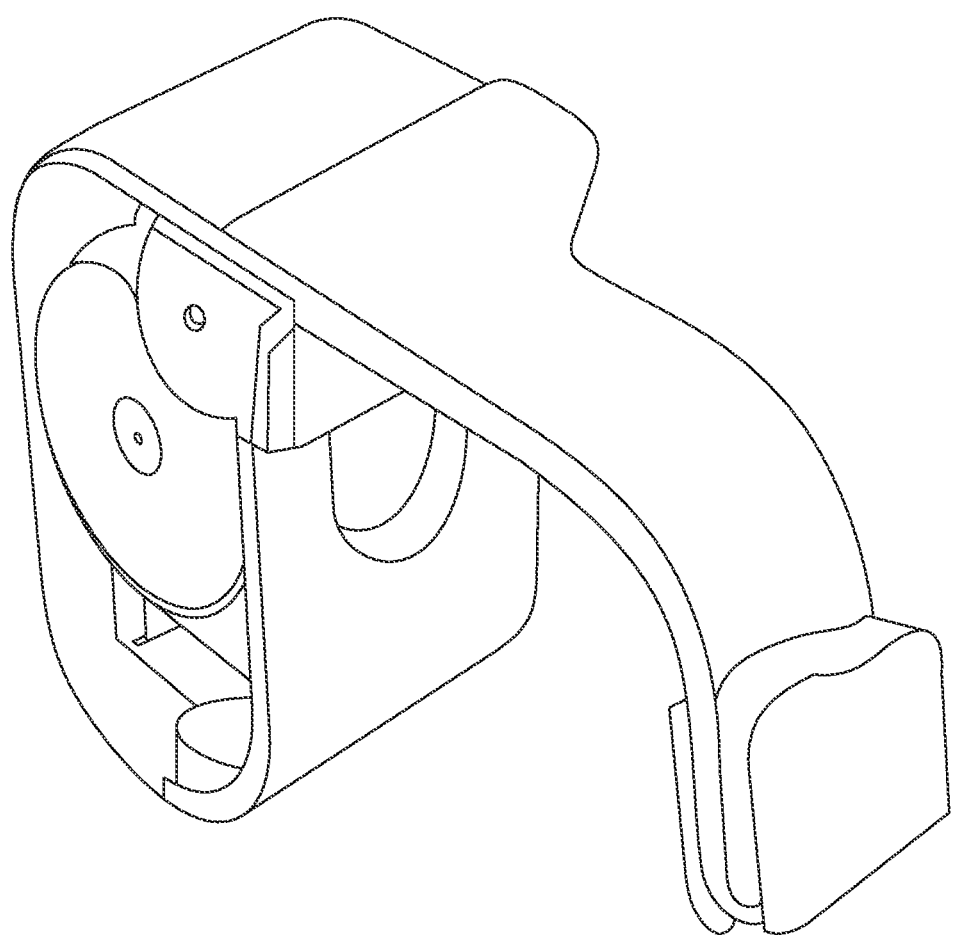
FIG. 3B is a drawing illustrating an example diagnostic hub for performing medical diagnostic tests for remote medicine, in accordance with one or more embodiments.

FIG. 3B is a drawing illustrating an example diagnostic hub for performing medical diagnostic tests for remote medicine, in accordance with one or more embodiments. The diagnostic hub is the same as or similar to the diagnostic hub 104 illustrated and described in more detail with reference to FIG. 1.

Figure 6:
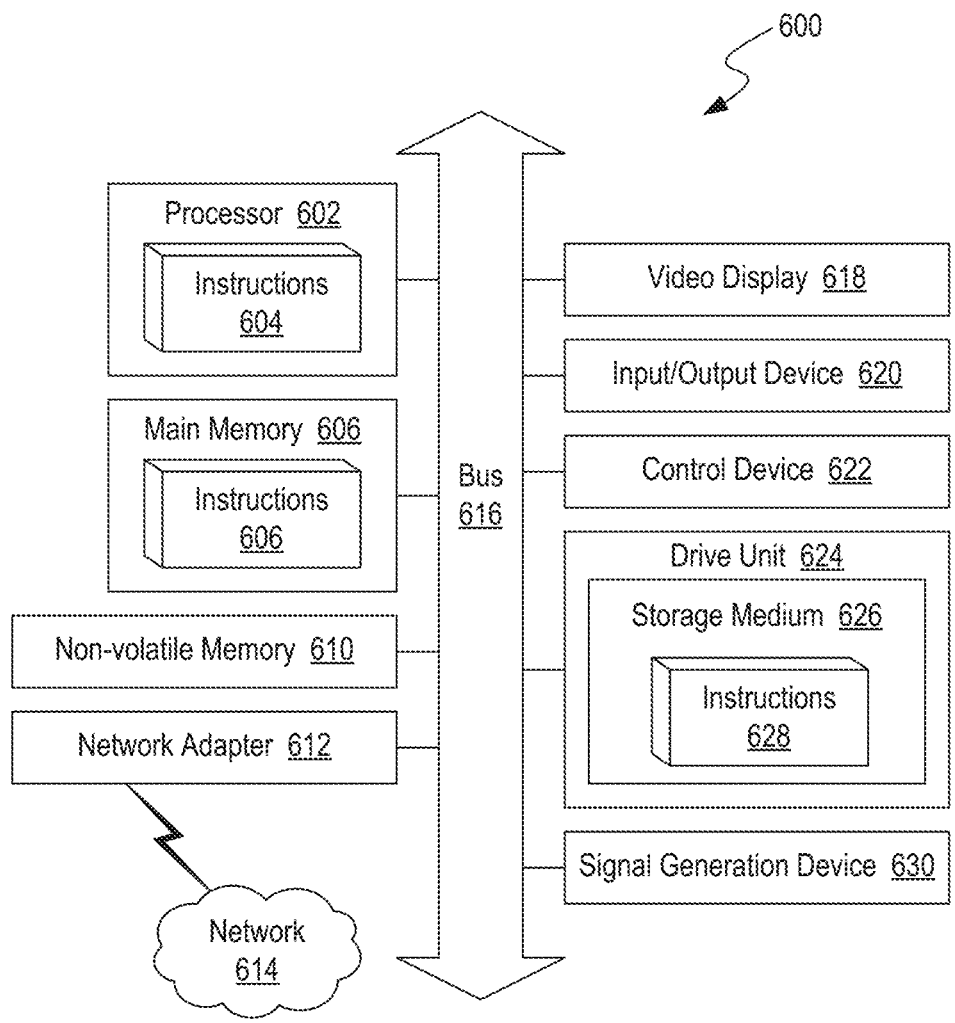
FIG. 6 is a block diagram illustrating an example computer system, in accordance with one or more embodiments.

FIG. 4 is a flow diagram illustrating an example process for performing medical diagnostic tests for remote medicine, in accordance with one or more embodiments. In some embodiments, the process of FIG. 4 is performed by the system 100 illustrated and described in more detail with reference to FIG. 1. In other embodiments, the process of FIG. 6 is performed by a computer system (e.g., the example computer system 600 illustrated and described in more detail with reference to FIG. 6). Particular entities, for example, the diagnostic hub 104, the ML system 700 or the ML model 716, perform some or all of the steps of the process in other embodiments. The diagnostic hub 104 is illustrated and described in more detail with reference to FIG. 1. The ML system 700 and the ML model 716 are illustrated and described in more detail with reference to FIG. 7. Likewise, embodiments can include different and/or additional steps, or perform the steps in different orders.

In embodiments, a wireless transceiver of the diagnostic hub 104, receives wireless communication signals from a mobile device of a user. An example wireless transceiver 108, example wireless communication signals 152, and example mobile device 148 are illustrated and described in more detail with reference to FIG. 1. For example, in step 404, the wireless transceiver 108, receives signals (e.g., wireless communication signals 152) emitted by a user device (e.g., the mobile device 148) in proximity to the diagnostic hub 104. The signals indicate an identity of the user device.

In embodiments, one or more computer processors 112 determine that the user is proximate to a toilet 144 based on the wireless communication signals 152. The one or more computer processors 112 and the toilet 144 are illustrated and described in more detail with reference to FIG. 1. For example in step 408, computer processors 112 determine that the user is in proximity to the diagnostic hub 104 based on the signals. The computer processors 112 can determine a user identification of the user based on the wireless communication signals 152. The computer processors 112 can determine a geolocation of the diagnostic hub 104 by analyzing location signals received by a geolocation receiver (e.g., geolocation receiver 214) of the diagnostic hub 104. The geolocation receiver 214 are illustrated and described in more detail with reference to FIG. 2. The computer processors 112 can determine a geolocation of the diagnostic hub 104 by analyzing location information embedded in the wireless communication signals 152. The diagnostic hub 104 can receive sensor data 164 generated by multiple biometric sensors and environmental sensors 168 communicably coupled to the diagnostic hub 104.

In embodiments, the diagnostic hub 104 is caused to intake a mixture 140 of water and urine and/or feces from the toilet 144 into an intake chamber 124 of the diagnostic hub 104 through an inlet line or one or more openings in a housing of the diagnostic hub 104. The mixture 140, toilet 144, and intake chamber 124 are illustrated and described in more detail with reference to FIG. 1. For example, in step 412, the computer processors 112 cause the diagnostic hub 104 to intake the mixture 140 from a bowl 136 of the toilet 144 into the housing of the diagnostic hub 104. The bowl 136 are illustrated and described in more detail with reference to FIG. 1. The housing can be located on a surface of the bowl 136, proximate to a water level in the bowl 136 or at least partially submerged in the bowl 136.

In embodiments, a lab-on-a-chip 116 of the diagnostic hub 104 analyzes the mixture 140. The analysis is performed by a biochemical assay on a fluid volume 128 of the mixture 140 using a reagent stored in the diagnostic hub 104. The fluid volume 128 are illustrated and described in more detail with reference to FIG. 1. The lab-on-a-chip 116 determines multiple substance levels present in the urine based on the biochemical assay. The lab-on-a-chip 116 generates results based on the multiple substance levels. The results can indicate a diagnosis of one or more diseases or medical conditions of the user. Diagnosis can refer to identifying the cause of a health problem after the onset of symptoms. For example, at-home tests can detect infectious diseases, such as COVID-19. After receiving the results, a doctor can formally diagnose a health condition, and may need to conduct additional tests to confirm the results of at-home testing.

The results can be used for screening or can indicate a likelihood that the user will develop a disease or medical condition. Screening refers to looking for signs of a health problem before any symptoms have occurred. For example, at-home testing can look for sexually transmitted diseases (STDs) that may not cause symptoms, thus helping to avoid the unknowing spread of the disease to others. The results can be used for disease assessment or wellness optimization. Disease risk assessment involves, in some situations, testing that can reveal when a person has a higher risk of developing a disease. For instance, some genetic tests can look for DNA mutations associated with certain types of cancer, such as BRCA gene mutations linked to an increased risk of breast and ovarian cancer. Wellness optimization involves helping users understand one or more aspects of their physical, mental, or emotional wellness. Some tests are designed not to look for a specific problem, but to offer more information about the user's body by, for example, measuring hormones, nutrient levels, or other substances.

The results can indicate a change in a level of the disease or medical condition in the user. For example, the results can be used for monitoring. Monitoring involves tracking how a person's health changes over time or in response to treatment. At-home kits that allow people with diabetes to measure their blood sugar are an example of monitoring. The results can indicate a substance level of a controlled substance present in the urine that is greater than a threshold substance level. For example, in step 416, the mixture 140 is analyzed using the lab-on-a-chip 116 by conducting a biochemical assay on the mixture 140, determining multiple substance levels present in the urine, and generating results. The computer processors 112 can correlate the results to the sensor data 164.

In step 420, the wireless transceiver 108 sends the correlated results 184 tagged by the user identification and the geolocation to the mobile device 148, a healthcare provider's device 180, and/or a cloud server 172.

Figure 5:
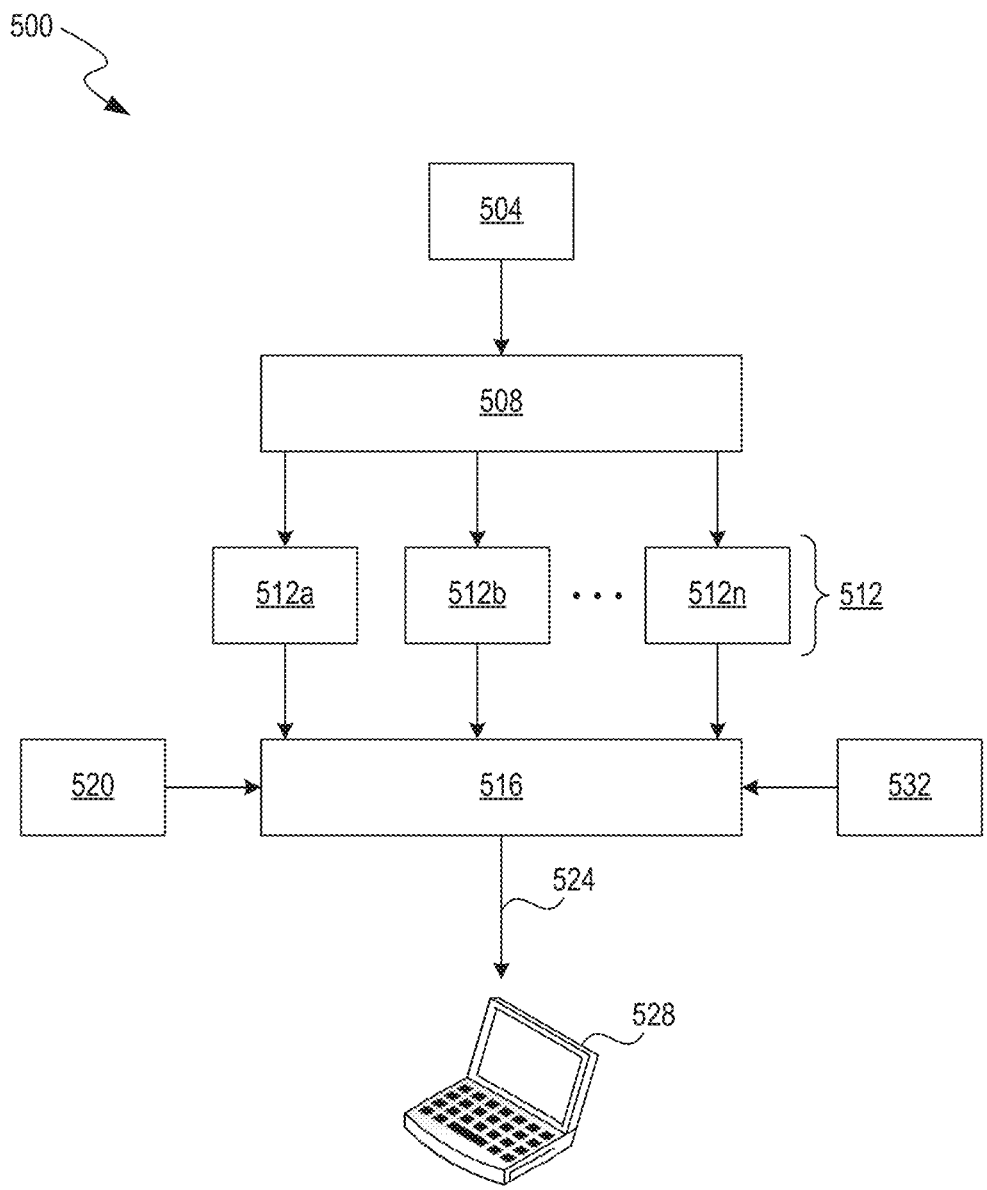
FIG. 5 is a block diagram illustrating an example machine learning (ML) system, in accordance with one or more embodiments.

FIG. 5 is a block diagram illustrating an example machine learning system 500, in accordance with one or more embodiments. The ML system 500 is implemented using components of the example computer system 600 illustrated and described in more detail with reference to FIG. 6. For example, the ML system 500 can be implemented on the console 708 using instructions programmed in the memory 764 illustrated and described in more detail with reference to FIG. 7. Likewise, embodiments of the ML system 500 can include different and/or additional components or be connected in different ways. The ML system 500 is sometimes referred to as an ML module.

The ML system 500 includes a feature extraction module 508 implemented using components of the example computer system 600 illustrated and described in more detail with reference to FIG. 6. In some embodiments, the feature extraction module 508 extracts a feature vector 512 from input data 504. For example, the input data 504 can include one or more physiological parameters measured by the monitors 712 illustrated and described in more detail with reference to FIG. 7. The feature vector 512 includes features 512a, 512b, . . . , 512n. The feature extraction module 508 reduces the redundancy in the input data 504 (e.g., repetitive data values), to transform the input data 504 into the reduced set of features 512 (e.g., features 512a, 512b, . . . , 512n). The feature vector 512 contains the relevant information from the input data 504, such that events or data value thresholds of interest can be identified by the ML model 516 by using this reduced representation. In some example embodiments, the following dimensionality reduction techniques are used by the feature extraction module 508: independent component analysis, isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 516 performs deep learning (also known as deep structured learning or hierarchical learning) directly on the input data 504 to learn data representations, as opposed to using task-specific algorithms. In deep learning, no explicit feature extraction is performed; the features 512 are implicitly extracted by the ML system 500. For example, the ML model 516 can use a cascade of multiple layers of nonlinear processing units for implicit feature extraction and transformation. Each successive layer uses the output from the previous layer as input. The ML model 516 can thus learn in supervised (e.g., classification) and/or unsupervised (e.g., pattern analysis) modes. The ML model 516 can learn multiple levels of representations that correspond to different levels of abstraction, wherein the different levels form a hierarchy of concepts. In this manner, the ML model 516 can be configured to differentiate features of interest from background features.

In alternative example embodiments, the ML model 516 (e.g., in the form of a CNN), generates the output 524, without the need for feature extraction, directly from the input data 504. The output 524 is provided to the computer device 528 or the console 708 illustrated and described in more detail with reference to FIG. 7. The computer device 528 is a server, computer, tablet, smartphone, smart speaker, etc., implemented using components of the example computer system 600 illustrated and described in more detail with reference to FIG. 6. In some embodiments, the steps performed by the ML system 500 are stored in memory on the computer device 528 for execution. In other embodiments, the output 524 is displayed on the high-definition monitors 524 illustrated and described in more detail with reference to FIG. 7.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 516 can be a CNN that includes both convolutional layers and max pooling layers. The architecture of the ML model 516 can be "fully convolutional," which means that variable-sized sensor data vectors can be fed into it. For all convolutional layers, the ML model 516 can specify a kernel size, a stride of the convolution, and an amount of zero padding applied to the input of that layer. For the pooling layers, the ML model 516 can specify the kernel size and stride of the pooling.

In some embodiments, the ML system 500 trains the ML model 516, based on the training data 520, to correlate the feature vector 512 to expected outputs in the training data 520. As part of the training of the ML model 516, the ML system 500 forms a training set of features and training labels by identifying a positive training set of features that have been determined to have a desired property in question, and, in some embodiments, forms a negative training set of features that lack the property in question.

The ML system 500 applies ML techniques to train the ML model 516 that, when applied to the feature vector 512, outputs indications of whether the feature vector 512 has an associated desired property or properties, such as a probability that the feature vector 512 has a particular Boolean property, or an estimated value of a scalar property. The ML system 500 can further apply dimensionality reduction (e.g., via linear discriminant analysis (LDA), PCA, or the like) to reduce the amount of data in the feature vector 512 to a smaller, more representative set of data.

The ML system 500 can use supervised ML to train the ML model 516, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 532 is formed of additional features, other than those in the training data 520, which have already been determined to have or to lack the property in question. The ML system 500 applies the trained ML model 516 to the features of the validation set 532 to quantify the accuracy of the ML model 516. Common metrics applied in accuracy measurement include: Precision and Recall, where Precision refers to a number of results the ML model 516 correctly predicted out of the total it predicted, and Recall is a number of results the ML model 516 correctly predicted out of the total number of features that had the desired property in question. In some embodiments, the ML system 500 iteratively re-trains the ML model 516 until the occurrence of a stopping condition, such as the accuracy measurement indication that the ML model 516 is sufficiently accurate, or a number of training rounds having taken place. The validation set 532 can include data corresponding to confirmed anatomical features, tissue states, tissue conditions, diagnoses, or combinations thereof. This allows the detected values to be validated using the validation set 532. The validation set 532 can be generated based on analysis to be performed.

FIG. 6 is a block diagram illustrating an example computer system 600, in accordance with one or more embodiments. Components of the example computer system 600 can be used to implement the monitors 712, the console 708, or the EHR database 706 illustrated and described in more detail with reference to FIG. 7. In some embodiments, components of the example computer system 600 are used to implement the ML system 700 illustrated and described in more detail with reference to FIG. 7. At least some operations described herein can be implemented on the computer system 600.

The computer system 600 can include one or more central processing units ("processors") 602, main memory 606, non-volatile memory 610, network adapters 612 (e.g., network interface), video displays 818, input/output devices 620, control devices 622 (e.g., keyboard and pointing devices), drive units 824 including a storage medium 626, and a signal generation device 830 that are communicatively connected to a bus 616. The bus 616 is illustrated as an abstraction that represents one or more physical buses and/or point-to-point connections that are connected by appropriate bridges, adapters, or controllers. The bus 616, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C)

bus, or an Institute of Electrical and Electronics Engineers (IEEE) standard 1394 bus (also referred to as "Firewire").

The computer system 600 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the computer system 600.

While the main memory 606, non-volatile memory 610, and storage medium 626 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 628. The term "machine-readable medium" and "storage medium" shall also be taken to include any medium that is capable of storing, encoding, or carrying a set of instructions for execution by the computer system 600.

In general, the routines executed to implement the embodiments can be implemented as part of an operating system or a specific application, component, program, object, module, or sequence of instructions (collectively referred to as "computer programs"). The computer programs typically include one or more instructions (e.g., instructions 604, 608, 628) set at various times in various memory and storage devices in a computer device. When read and executed by the one or more processors 602, the instruction(s) cause the computer system 600 to perform operations to execute elements involving the various aspects disclosed herein.

Moreover, while embodiments have been described in the context of fully functioning computer devices, those skilled in the art will appreciate that the various embodiments are capable of being distributed as a program product in a variety of forms. The techniques are applicable regardless of the particular type of machine or computer-readable media used to actually effect the distribution.

Further examples of machine-readable storage media, machine-readable media, or computer-readable media include recordable-type media, such as volatile and non-volatile memory devices 610, floppy and other removable disks, hard disk drives, optical discs (e.g., Compact Disc Read Only Memory (CD-ROMS), Digital Versatile Discs (DVDs)), and transmission-type media, such as digital and analog communication links.

The network adapter 612 enables the computer system 600 to mediate data in a network 614 with an entity that is external to the computer system 600 through any communication protocol supported by the computer system 600 and the external entity. The network adapter 612 can include a network adapter card, a wireless network interface card, a router, an access point, a wireless router, a switch, a multi-layer switch, a protocol converter, a gateway, a bridge, a bridge router, a hub, a digital media receiver, and/or a repeater.

The network adapter 612 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions, including the access and operation rights of an object by an individual, a machine, and/or an application, and the circumstances under which the permission rights stand.

Figure 7:
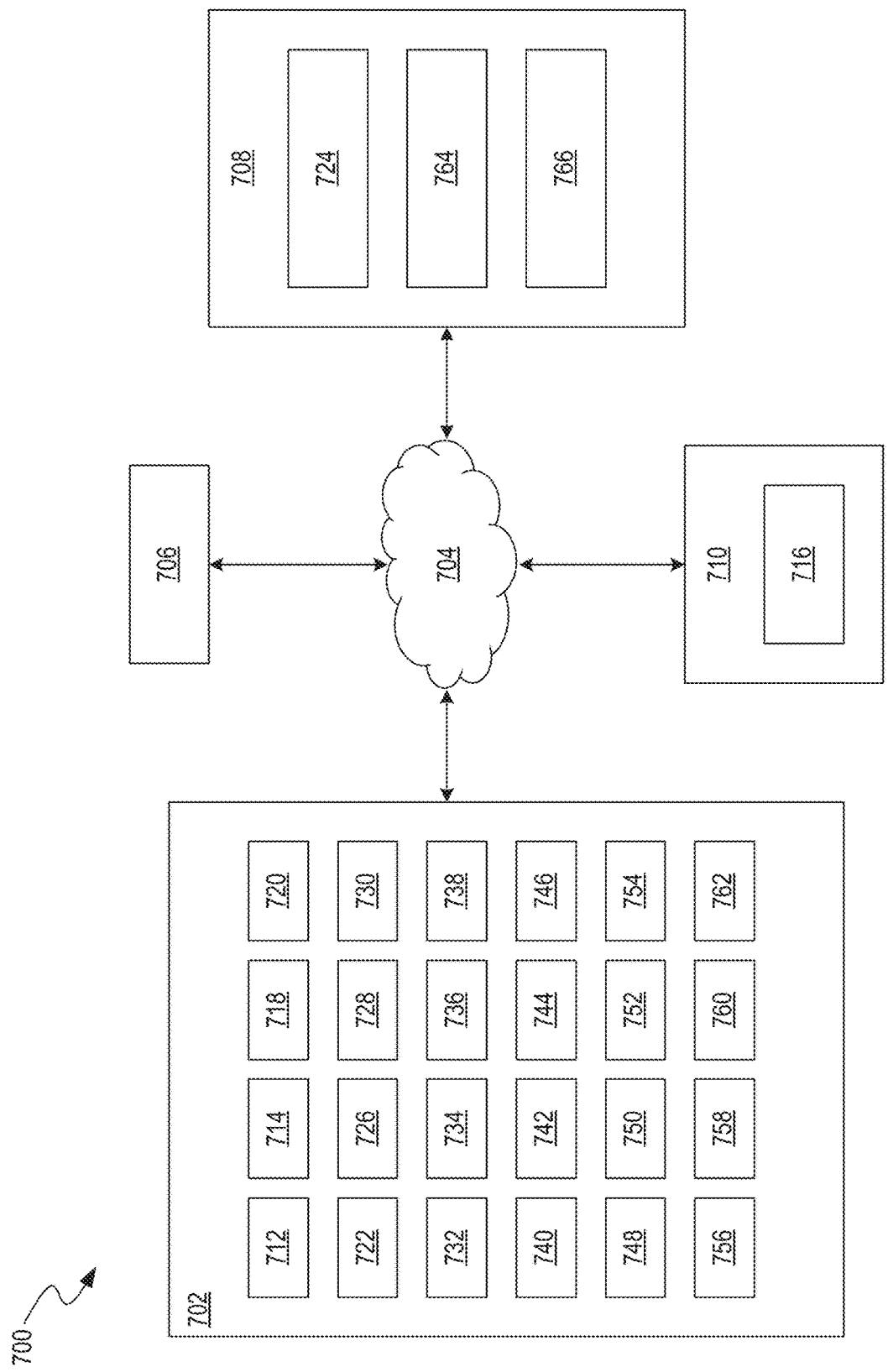
FIG. 7 is a block diagram illustrating an example system for enabling medical diagnostic tests for remote medicine, in accordance with one or more embodiments.

FIG. 7 is a block diagram illustrating an example system 700 for enabling medical diagnostic tests for remote medicine, in accordance with one or more embodiments. The system 700 includes various surgical and medical equipment (e.g., a patient monitor 712) located within an operating room 702 or a doctor's office 710, a console 708 for performing surgery or other patient care, and a database 706 for storing electronic health records. The system 700 is implemented using the components of the example computer system 600 illustrated and described in more detail with reference to FIG. 6. Likewise, embodiments of the system 700 can include different and/or additional components or can be connected in different ways.

The operating room 702 is a facility, for example, within a hospital, where surgical operations are carried out in an aseptic environment. Proper surgical procedures require a sterile field. In some embodiments, the sterile field is maintained in the operating room 702 in a medical care facility, such as a hospital, the doctor's office 710, or an outpatient surgery center.

In some embodiments, the system 700 includes one or more medical or surgical patient monitors 712. The monitors 712 can include a vital signs monitor (a medical diagnostic instrument), which can be a portable, battery-powered, multi-parametric, vital signs monitoring device used for both ambulatory and transport applications, as well as bedside monitoring. The vital signs monitor can be used with an isolated data link to an interconnected portable computer or the console 708, allowing snapshot and trended data from the vital signs monitor to be printed automatically at the console 708, and also allowing default configuration settings to be downloaded to the vital signs monitor. The vital signs monitor is capable of use as a stand-alone unit, as well as part of a bi-directional wireless communications network that includes at least one remote monitoring station (e.g., the console 708). The vital signs monitor can measure multiple physiological parameters of a patient wherein various sensor output signals are transmitted either wirelessly or by means of a wired connection to at least one remote site, such as the console 708.

In some embodiments, the monitors 712 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate (e.g., number of beats, strength of beats, regularity of beats, beat anomalies, etc.).

In some embodiments, the monitors 712 include a pulse oximeter or $SpO_2$ monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 712 include an end-tidal $CO_2$ monitor or capnography monitor used for measurement of the level of carbon dioxide that is released at the end of an exhaled breath (referred to as end-tidal carbon dioxide, $ETCO_2$). An $ETCO_2$ monitor or capnography monitor is widely used in anesthesia and intensive care. $ETCO_2$ can be calculated by plotting expiratory $CO_2$ with time. Further, $ETCO_2$ monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The $ETCO_2$ monitor can be configured as side stream (diverting) or mainstream (non-diverting). A diverting $ETCO_2$ monitor transports a portion of a patient's respired gases from the sampling site to the $ETCO_2$ monitor, while a non-diverting $ETCO_2$ monitor does not transport gas away. Also, measurement by the $ETCO_2$ monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 712 include a blood pressure monitor that measures blood pressure, particularly in arteries. The blood pressure monitor uses a non-invasive technique (by external cuff application) or an invasive technique (by a cannula needle inserted in an artery, used in the operating room 702) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 712 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 712 measure respiration rate or breathing rate—the rate at which breathing occurs- and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 712 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 712 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 712 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 712 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 712 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 712 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 712 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 712 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an augmented reality device like Google Glass™, or cameras are integrated into an endoscopic, microscopic, or laparoscopic device. In some embodiments, a camera or other imaging device (e.g., ultrasound) present in the operating room 702 is associated with one or more areas in the operating room 702. The sensors can be associated with measuring a specific parameter of the patient, such as respiratory rate, blood pressure, blood oxygen level, heart rate, etc.

In some embodiments, the system 700 includes a medical visualization apparatus 714 used for visualization and analysis of objects (preferably two-dimensional (2D) or three-dimensional (3D) objects) in the operating room 702. The medical visualization apparatus 714 provides the selection of points at surfaces, selection of a region of interest, or selection of objects. The medical visualization apparatus 714 can also be used for diagnosis, treatment planning, intraoperative support, documentation, or educational purposes. The medical visualization apparatus 714 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 700 includes an instrument 718 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery, such as for removing polyps from the colon. An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 700 includes fiber optics 720, which refer to flexible, transparent fiber made by drawing glass (silica) or plastic to a diameter slightly thicker than that of a human hair. Fiber optics 720 are arranged in bundles called optical cables and used to transmit light signals across long distances. Fiber optics 720 are used most often as a means to transmit light between the two ends of the fiber and find wide usage in the medical field. Traditional surgery requires sizable and invasive incisions to expose internal organs and operate on affected areas, but with fiber optics 720 much smaller surgical incisions can be performed. Fiber optics 720 contain components such as a core, cladding, and buffer coating. Fiber optics 720 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 700 includes surgical lights 722 (referred to as operating lights) that perform illumination of a local area or cavity of the patient. Surgical lights 722 play an important role in illumination before, during, and after a medical procedure. Surgical lights 722 can be categorized by lamp type as conventional (incandescent) and LED (light-emitting diode). Surgical lights 722 can be categorized by mounting configuration as ceiling-mounted, wall-mounted, or floor stand. Surgical lights 722 can be categorized by type as tungsten, quartz, xenon halogens, and/or LEDs. Surgical lights 722 include sterilizable handles, which allow a surgical robot to adjust light positions. Some important factors affecting surgical lights 722 can be illumination, shadow management (cast shadows and contour shadows), the volume of light, heat management, or fail-safe surgical lighting.

In some embodiments, the system 700 includes a surgical tower 728 (e.g., used in conjunction with the robotic surgical system 760 disclosed herein) for MIS. The surgical tower 728 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 728 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 728 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 700 includes an instrument 730 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 730 can be used. For example, after removing part of the liver for removal of a tumor, etc., blood vessels in the liver must be sealed individually. The electrocautery instrument 730 can be used for sealing living tissue such as arteries, veins, lymph nodes, nerves, fats, ligaments, and other soft tissue structures. The electrocautery instrument 730 can be used in applications such as surgery, tumor removal, nasal treatment, or wart removal. Electrocautery can operate in two modes, monopolar or bipolar. The electrocautery instrument 730 can consist of a generator, a handpiece, and one or more electrodes.

In some embodiments, the system 700 includes a laser 732 used in association with MIS devices. The laser 732 can be used in MIS with an endoscope. The laser 732 is attached to the distal end of the endoscope and steered at high speed by producing higher incision quality than with existing surgical tools thereby minimizing damage to surrounding tissue. The laser 732 can be used to perform MIS using a laparoscope in the lower and upper gastrointestinal tract, eye, nose, and throat. The laser 732 is used in MIS to ablate soft tissues, such as a herniated spinal disc bulge.

In some embodiments, sensors 734 are used in association with MIS devices and the robotic surgical system 760 described herein. The sensors 734 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 734 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 734 can output shape, size, pressure, softness, composition, temperature, vibration, shear, and normal forces. The sensors 734 can be electrical or optical, consisting of capacitive, inductive, piezoelectric, piezoresistive, magnetic, and auditory. The sensors 734 can be used in robotic or laparoscopic surgery, palpation, biopsy, heart ablation, and valvuloplasty.

In some embodiments, the system 700 includes an imaging system 736 (instruments are used for the creation of images and visualization of the interior of a human body for diagnostic and treatment purposes). The imaging system 736 is used in different medical settings and can help in the screening of health conditions, diagnosing causes of symptoms, or monitoring of health conditions. The imaging system 736 can include various imaging techniques, such as X-ray, fluoroscopy, magnetic resonance imaging (MRI), ultrasound, endoscopy, elastography, tactile imaging, thermography, medical photography, and nuclear medicine, for example, positron emission tomography (PET). Some factors which can drive the market are cost and clinical advantages of medical imaging modalities, a rising share of aging populations, increasing prevalence of cardiovascular or lifestyle diseases, and increasing demand from emerging economies.

In some embodiments, the imaging system 736 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 736 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 736 uses computed tomography imaging (CT) that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images- or "slices"— of the body. A CT instrument is different from an X-ray instrument as it creates three-dimensional cross-sectional images of the body, while the X-ray instrument creates two-dimensional images of the body. The three-dimensional cross-sectional images are created by taking images from different angles, which is done by taking a series of tomographic images from different angles. The diverse images are collected by a computer and digitally stacked to form a three-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 736 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 736 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs, such as liver/kidneys/pancreas, fetal monitoring, etc.) in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 700 includes a stereotactic navigation system 738 that uses patient imaging (e.g., CT, MRI) to guide surgical robots in the placement of specialized surgical instruments and implants. The patient images are taken to guide a surgical robot before or during the medical procedure. The stereotactic navigation system 738 includes a camera having infrared sensors to determine the location of the tip of the probe being used in the surgical procedure. This information is sent in real-time so that the surgical robot has a clear image of the precise location where it is working in the body. The stereotactic navigation system 738 can be framed (requires attachment of a frame to the patient's head using screws or pins) or frameless (does not require the placement of a frame on the patient's anatomy). The stereotactic navigation system 738 can be used for diagnostic biopsies, tumor resection, bone preparation/implant placement, placement of electrodes, otolaryngologic procedures, or neurosurgical procedures.

In some embodiments, the system 700 includes an anesthesiology machine 740 that is used to generate and mix medical gases, such as oxygen or air, and anesthetic agents to induce and maintain anesthesia in patients. The anesthesiology machine 740 delivers oxygen and anesthetic gas to the patient and filters out expiratory carbon dioxide. The anesthesiology machine 740 can perform functions such as providing oxygen (02), accurately mixing anesthetic gases and vapors, enabling patient ventilation, and minimizing anesthesia-related risks to patients and staff. The anesthesiology machine 140 can include the following essential components: a source of $O_2$, $O_2$ flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 740 can be divided into three parts: the high pressure system, the intermediate pressure system, and the low pressure system. The process of anesthesia starts with oxygen flow from a pipeline or cylinder through the flowmeter; the 02 flows through the vaporizer and picks up the anesthetic vapors; the $O_2$-anesthetic mix then flows through the breathing circuit and into the patient's lungs, usually by spontaneous ventilation or normal respiration.

In some embodiments, the system 700 includes a surgical bed 742 equipped with mechanisms that can elevate or lower the entire bed platform; flex, or extend individual components of the platform; or raise or lower the head or the feet of the patient independently. The surgical bed 742 can be an operation bed, cardiac bed, amputation bed, or fracture bed. Some essential components of the surgical bed 742 can be a bed sheet, woolen blanket, bath towel, and bed block. The surgical bed 742 can also be referred to as a post-operative bed, which refers to a special type of bed made for the patient who is coming from the operation theater or from another procedure that requires anesthesia. The surgical bed 742 is designed in a manner that makes it easier to transfer an unconscious or weak patient from a stretcher/wheelchair to the bed. The surgical bed 742 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 700 includes a Jackson frame 744 (or Jackson table), which refers to a frame or table that is designed for use in spinal surgeries and can be used in a variety of spinal procedures in supine, prone, or lateral positions in a safe manner. Two peculiar features of the Jackson table 744 are the absence of central table support and an ability to rotate the table through 180 degrees. The Jackson table 744 is supported at both ends, which keeps the whole of the table free. This allows the visualization of a patient's trunk and major parts of extremities as well. The Jackson frame 744 allows the patient to be slid from the cart onto the table in the supine position with appropriate padding placed. The patient is then strapped securely on the Jackson table 744.

In some embodiments, the system 100 includes a disposable air warmer 746 (sometimes referred to as a Bair™ or Bair Hugger™). The disposable air warmer 746 is a convective temperature management system used in a hospital or surgery center to maintain a patient's core body temperature. The disposable air warmer 746 includes a reusable warming unit and a single-use disposable warming blanket for use during surgery. It can also be used before and after surgery. The disposable air warmer 746 uses convective warming consisting of two components: a warming unit and a disposable blanket. The disposable air warmer 746 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 700 includes a sequential compression device (SCD) 748 used to help prevent blood clots in the deep veins of legs. The sequential compression device 748 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 748 can be discomfort, warmth, sweating beneath the cuff, skin breakdown, nerve damage, or pressure injury.

In some embodiments, the system 700 includes a bed position controller 750, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 700 includes environmental controls 752. The environmental controls 752 can be operating room environmental controls for control or maintenance of the environment in the operating room 702 where procedures are performed to minimize the risk of airborne infection and to provide a conducive environment for everyone in the operating room 702 (e.g., surgeon, anesthesiologist, nurses, and patient). Some factors that can contribute to poor quality in the environment of the operating room 702 are temperature, ventilation, and humidity, and those conditions can lead to profound effects on the health and work productivity of people in the operating room 702. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 752 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 702. The operating room 702 can be a traditional operating room (which can have a large diffuser array directly above the operating table) or a hybrid operating room (which can have monitors and imaging equipment 736 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 752 include an air purification system for removing contaminants from the air in the operating room 702 to improve indoor air quality. Air purification can be important in the operating room 702 as surgical site infection can be a reason for high mortality and morbidity. The air purification system can deliver clean, filtered, contaminant-free air over the surgical bed 742 using a diffuser, airflow, etc., to remove all infectious particles down and away from the patient. The air purification system can be an air curtain, multi-diffuser array, or single large diffuser (based on laminar diffuser flow) or high-efficiency particulate air filter (HEPA filter). A HEPA filter protects a patient from infection and contamination using a filter, which is mounted at the terminal of the duct. A HEPA filter can be mounted on the ceiling and deliver clean, filtered air in a flow to the operating room 702 that provides a sweeping effect that pushes contaminants out via the return grilles that are usually mounted on the lower wall.

In some embodiments, the system 700 includes one or more medical or surgical tools 754. The surgical tools 754 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, elbow, arthroscopic, hip, and knee. The orthopedic tools can be fixation tools, relieving tools, corrective tools, or compression-distraction tools. A fixation tool refers to a tool designed to restrict movements partially or completely in a joint, for example, hinged splints (for preserving a certain range of movement in a joint) or rigid splints. A relieving tool refers to a tool designed to relieve pressure on an ailing part by transferring support to healthy parts of an extremity (e.g., Thomas splint and the Voskoboinikova apparatus). A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities (e.g., curvature, shortening, and pseudarthrosis such as Gudushauri). A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 754 include a drill for making holes in bones for insertion of implants such as nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit.

In some embodiments, the surgical tools 754 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery, (e.g., complications such as nerve thermal injury, grasping soft tissue, tearing dura mater, and mechanical injury).

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 754 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. Medical equipment refers to an article, instrument, apparatus, or machine used for diagnosis, prevention, or treatment of a medical condition or disease, or for the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 756 to aid in breathing. The machine 756 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks, such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 756 is a continuous positive airway pressure (CPAP) instrument used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 700 includes surgical supplies, consumables 758, or necessary supplies for the system 700 to provide care within the hospital or surgical environment. The consumables 758 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 758 can be disposable (e.g., time-saving, have no risk of healthcare-associated infections, and cost-efficient) or sterilizable (to avoid cross-contamination or risk of surgical site infections).

In some embodiments, the system 700 includes a robotic surgical system 760 (sometimes referred to as a medical robotic system or a robotic system) that provides intelligent services and information to the operating room 702 and the console 708 by interacting with the environment, including human beings, via the use of various sensors, actuators, and human interfaces. The robotic surgical system 760 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 766 at the console 708), which use the surgeon's actions on one side to control one or more "effectors" on the other side. The medical robotic system 760 provides precision and can be used for remotely controlled, minimally invasive procedures. The robotic surgical system 760 includes computer-controlled electromechanical devices that work in response to controls (e.g., input devices 766 at the console 708) manipulated by the surgeons.

In some embodiments, the system 700 includes equipment tracking systems 762, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, NFC, Wi-Fi, etc. The equipment tracking system 762 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 762 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 700 includes medical equipment, computers, software, etc., located in the doctor's office 710 that is communicably coupled to the operating room 702 over the network 704. For example, the medical equipment in the doctor's office 710 can include a microscope 716 used for viewing samples and objects that cannot be seen with an unaided eye. The microscope 716 can have components such as eyepieces, objective lenses, adjustment knobs, a stage, an illuminator, a condenser, or a diaphragm. The microscope 716 works by manipulating how light enters the eye using a convex lens, where both sides of the lens are curved outwards. When light reflects off of an object being viewed under the microscope 716 and passes through the lens, it bends toward the eye. This makes the object look bigger than it is. The microscope 716 can be compound (light-illuminated and the image seen with the microscope 716 is two-dimensional), dissection or stereoscope (light-illuminated and the image seen with the microscope 716 is three-dimensional), confocal (laser-illuminated and the image seen with the microscope 716 is on a digital computer screen), scanning electron (SEM) (electron-illuminated and the image seen with the microscope 716 is in black and white), or transmission electron microscope (TEM) (electron-illuminated and the image seen with the microscope 716 is the high magnification and high resolution).

The system 700 includes an electronic health records (EHR) database 706 that contains patient records. The EHR is a digital version of patients' paper charts. The EHR database 706 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 706. Electronic health records can also include data collected from the monitors 712 from historical procedures. The EHR database 706 is implemented using components of the example computer system 600 illustrated and described in more detail with reference to FIG. 6.

In some embodiments, the EHR database 706 includes a digital record of patients' health information, collected, and stored systematically over time. The EHR database 706 can include demographics, medical history, history of present illness (HPI), progress notes, problems, medications, vital signs, immunizations, laboratory data, or radiology reports. Software (in memory 764) operating on the console 708 or implemented on the example computer system 600 (e.g., the instructions 604, 608 illustrated and described in more detail with reference to FIG. 6) are used to capture, store, and share patient data in a structured way. The EHR database 706 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 706 can also be used to facilitate clinical research by combining patients' demographics into a large pool. For example, the EHR database 706 can support a wide range of epidemiological research on the natural history of disease, drug utilization, and safety, as well as health services research.

The console 708 is a computer device, such as a server, computer, tablet, smartphone, smart speaker, etc., implemented using components of the example computer system 600 illustrated and described in more detail with reference to FIG. 6. In some embodiments, the steps for each procedure disclosed herein are stored in memory 764 on the console 708 for execution.

In some embodiments, the operating room 702 or the console 708 includes high-definition monitors 724, which refer to displays in which a clearer picture is possible than with low-definition, low-resolution screens. The high-definition monitors 724 have a higher density of pixels per inch than past standard TV screens. Resolution for the high-definition monitors 724 can be 1280×720 pixels or more (e.g., full HD, 1920×1080; quad HD, 2560×1440; 4K, 3840×2160; 8K, 7680×4320 pixels). The high-definition monitor 724 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 708 includes an input interface or one or more input devices 766. The input devices 766 can include a keyboard, a mouse, a joystick, any hand-held controller, or a hand-controlled manipulator (e.g., a tele-manipulator used to perform robotic surgery).

In some embodiments, the console 708, the equipment in the doctor's office 710, and the EHR database 706 are communicatively coupled to the equipment in the operating room 702 by a direct connection, such as ethernet, or wirelessly by the cloud over the network 704. The network 704 is the same as or similar to the network 614 illustrated and described in more detail with reference to FIG. 6. For example, the console 708 can communicate with the robotic surgical system 760 using the network adapter 612 illustrated and described in more detail with reference to FIG. 6.

The functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), FPGAs, etc.

The description and drawings herein are illustrative and are not to be construed as limiting. Numerous specific details are described to provide a thorough understanding of the disclosed methods and apparatus. However, in certain instances, well-known details are not described in order to avoid obscuring the description. Further, various modifications can be made without deviating from the scope of the embodiments.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

It is to be understood that the embodiments and variations shown and described herein are merely illustrative of the principles of this invention and that various modifications can be implemented by those skilled in the art.

I claim:

1. A computer-implemented method of operating a diagnostic hub located in a toilet, comprising:
   receiving, by a wireless transceiver of the diagnostic hub, a wireless signal from a mobile device;
   determining a user identification and that the mobile device is proximate to the toilet based on the wireless signal;
   determining a geolocation of the diagnostic hub by at least one of:

analyzing location signals received by a geolocation receiver of the diagnostic hub; or
analyzing location information in the wireless signal;
receiving sensor data generated by a plurality of biometric sensors and environmental sensors communicably coupled to the diagnostic hub;
causing the diagnostic hub to intake a mixture of water and at least one of urine or feces from the toilet into an intake chamber of the diagnostic hub through an inlet line or one or more openings in a housing of the diagnostic hub;
biosensing, by a lab-on-a-chip of the diagnostic hub, one or more micro ribonucleic acid (miRNA) biomarkers in the mixture using one or more biosensors of the lab-on-a-chip;
performing a biochemical assay on a fluid volume of the mixture, using a biochemical reagent, to produce one or more measurements of:
cellular processes or metabolic reactions; and
substances or functional activity of biomolecules;
performing an analysis, by one or more computer processors implemented in the diagnostic hub, by:
extracting a feature vector from the one or more miRNA biomarkers and the one or more measurements; and
determining, using at least one machine learning model, from the feature vector, at least one of:
a diagnosis of one or more diseases or medical conditions of a user;
a likelihood that the user will develop the one or more diseases or medical conditions;
a likelihood that the user will develop a more severe or more mild form of one more diseases or medical conditions;
pre-existing conditions or risk factors for other diseases or medical conditions; or
a change in severity of the one or more diseases or medical conditions in the user;
correlating the analysis to the sensor data; and
transmitting, by the wireless transceiver, the correlated analysis to the mobile device or a cloud server, wherein the correlated analysis is tagged by the user identification and the geolocation.

2. The method of claim 1, comprising:
determining, from the biochemical assay, a substance level of a controlled substance present in the at least one of urine or feces that is greater than a threshold substance level.

3. The method of claim 1, comprising:
increasing a frequency of transmitting the correlated analysis to the mobile device or the cloud server responsive to determining at least one of a particular indication in the analysis or a particular correlation of the analysis to the sensor data.

4. The method of claim 1, wherein the sensor data describes at least one of a heart rate, a blood pressure, an amount of dissolved oxygen, a respiratory rate, a composition of sweat, a stress level, or a body temperature of the user.

5. The method of claim 1, wherein the housing is located on a surface of a bowl of the toilet and proximate to a water level in the bowl or at least partially submerged in water.

6. The method of claim 1, comprising storing the analysis in a user health database comprising trends recorded over time of:
a plurality of substance levels;
diagnoses of the one or more diseases or medical conditions;
likelihoods that the user will develop the one or more diseases or medical conditions;
the pre-existing conditions or risk factors for other diseases or medical conditions; or
changes in the severity of the one or more diseases or medical conditions in the user.

7. The method of claim 1, wherein the analysis is performed by the lab-on-a-chip on the mixture using a biochemical reagent.

8. The method of claim 1, wherein the biosensing is performed using at least one of a paper-based microfluidic device (µPAD), a digital microfluidic (DMF) device, or a lateral flow biosensor in the lab-on-a-chip.

9. The method of claim 1, wherein the biosensing is performed using a DNA sensor in the lab-on-a-chip and the one or more computer processors execute a pharmacogenetics application that considers drug metabolic pathways affecting one or more user's individual responses to a drug based on genetic information obtained using the DNA sensor.

10. The method of claim 1, wherein the lab-on-a-chip comprises at least one of a complementary metal oxide semiconductor (CMOS)-based DNA sensor, an AC electro-osmosis (ACEO) chip, or a label-free impedimetric DNA sensing chip.

11. A diagnostic hub located in a toilet, consisting of:
one or more computer processors; and
a non-transitory computer-readable storage medium storing computer instructions, which, when executed by the one or more computer processors, cause the diagnostic hub to:
receive, by a wireless transceiver, a wireless signal from a mobile device;
determine a user identification and that the mobile device is proximate to the toilet based on the wireless signal;
determine a geolocation by at least one of:
analyzing location signals received by a geolocation receiver; or
analyzing location information embedded in the wireless signal;
receive sensor data generated by a plurality of biometric sensors and environmental sensors communicably coupled to the diagnostic hub;
intake a mixture of water and at least one of urine or feces from the toilet into an intake chamber through an inlet line or one or more openings in a housing of the diagnostic hub;
perform an analysis, by a lab-on-a-chip, of the mixture by:
biosensing one or more micro ribonucleic acid (miRNA) biomarkers in the mixture using one or more biosensors; and
performing a biochemical assay to produce one or more measurements of:
cellular processes or metabolic reactions; and
substances or functional activity of biomolecules;
extract a feature vector from the one or more miRNA biomarkers and the one or more measurements;
determine, from the feature vector, one of:
a diagnosis of one or more diseases or medical conditions of a user;
a likelihood that the user will develop the one or more diseases or medical conditions; or a change in severity of the one or more diseases or medical conditions in the user;

correlate the analysis to the sensor data; and transmit, by the wireless transceiver, the correlated analysis to the mobile device or a cloud server, wherein the correlated analysis is tagged by the user identification and the geolocation.

12. The diagnostic hub of claim 11, wherein the computer instructions cause the diagnostic hub to determine, from the biochemical assay, a substance level of a controlled substance present in the at least one of urine or feces that is greater than a threshold substance level.

13. The diagnostic hub of claim 11, wherein the computer instructions cause the diagnostic hub to:

increase a frequency of transmitting the correlated analysis to the mobile device or the cloud server responsive to determining at least one of a particular indication in the analysis or a particular correlation of the analysis to the sensor data.

14. The diagnostic hub of claim 11, wherein the sensor data describes at least one of a heart rate, a blood pressure, an amount of dissolved oxygen, a respiratory rate, a composition of sweat, a stress level, or a body temperature of the user.

15. The diagnostic hub of claim 11, wherein the housing is located on a surface of a bowl of the toilet and proximate to a water level in the bowl or at least partially submerged in water.

16. The diagnostic hub of claim 11, wherein the computer instructions cause the diagnostic hub to store the analysis in a user health database consisting of trends recorded over time of:

diagnoses of the one or more diseases or medical conditions;

likelihoods that the user will develop the one or more diseases or medical conditions; or changes in the severity of the one or more diseases or medical conditions in the user.

17. The diagnostic hub of claim 11, wherein the biosensing is performed using a lateral flow biosensor in the lab-on-a-chip.

18. The diagnostic hub of claim 11, wherein the biosensing is performed using a paper-based microfluidic device (μPAD) in the lab-on-a-chip.

19. The diagnostic hub of claim 11, wherein the biosensing is performed using a digital microfluidic (DMF) device in the lab-on-a-chip.

20. A non-transitory computer-readable storage medium storing computer instructions, which, when executed by one or more computer processors, cause the one or more computer processors to:

receive, by a wireless transceiver, a wireless signal from a mobile device;

determine a user identification and that the mobile device is proximate to a toilet based on the wireless signal;

determine a geolocation by at least one of:

analyzing location signals received by a geolocation receiver; or analyzing location information embedded in the wireless signal;

receive sensor data generated by a plurality of biometric sensors and environmental sensors communicably coupled to a diagnostic hub;

intake a mixture of water and at least one of urine or feces from the toilet into an intake chamber through an inlet line or one or more openings in a housing of the diagnostic hub;

biosense, by a lab-on-a-chip, one or more micro ribonucleic acid (miRNA) biomarkers in the mixture using one or more biosensors;

perform a biochemical assay on a fluid volume of the mixture, using a biochemical reagent, to produce one or more measurements of:

cellular processes or metabolic reactions;

and substances or functional activity of biomolecules;

perform an analysis, by the one or more computer processors implemented in the diagnostic hub, by:

extracting a feature vector from the one or more miRNA biomarkers and the one or more measurements; and determining, using at least one machine learning model, from the feature vector, at least one of:

a diagnosis of one or more diseases or medical conditions of a user;

a likelihood that the user will develop the one or more diseases or medical conditions;

a likelihood that the user will develop a more severe or more mild form of one more diseases or medical conditions;

pre-existing conditions or risk factors for other diseases or medical conditions; or a change in severity of the one or more diseases or medical conditions in the user;

correlate the analysis to the sensor data; and transmit, by the wireless transceiver, the correlated analysis to the mobile device or a cloud server, wherein the correlated analysis is tagged by the user identification and the geolocation.

* * * * *